(12) United States Patent
Morard et al.

(10) Patent No.: US 11,227,683 B2
(45) Date of Patent: Jan. 18, 2022

(54) METHODS AND SYSTEMS FOR CHARACTERIZING ANATOMICAL FEATURES IN MEDICAL IMAGES

(71) Applicant: GE Precision Healthcare LLC, Milwaukee, WI (US)

(72) Inventors: Vincent Jerome Morard, Versailles (FR); Ronan Quelever, Le Chesnay (FR); Laura Dumont, Paris (FR); Nicolas Gogin, Chatenay Malabry (FR); Nicolas Coustaud, Versailles (FR); Luc Nicodeme, Meudon (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 16/750,931

(22) Filed: Jan. 23, 2020

(65) Prior Publication Data

US 2021/0233645 A1 Jul. 29, 2021

(51) Int. Cl.
*G16H 30/00* (2018.01)
*G16H 30/40* (2018.01)
(Continued)

(52) U.S. Cl.
CPC ........... *G16H 30/40* (2018.01); *G06K 9/6202* (2013.01); *G06K 9/6268* (2013.01); *G06N 3/084* (2013.01);
(Continued)

(58) Field of Classification Search
CPC .. G16H 30/40; G06T 7/38; G06T 7/11; G06T 7/174; G06T 7/0014; G06T 2207/10081;
(Continued)

(56) References Cited

U.S. PATENT DOCUMENTS

| 9,092,691 B1 | 7/2015 | Beaumont et al. |
| 2007/0127789 A1* | 6/2007 | Hoppel ................ A61B 6/5247 382/128 |

(Continued)

OTHER PUBLICATIONS

Sun et al. Automatic segmentation of liver tumors from multiphase contrast-enhanced CT images based on FCNs, Artificial Intelligence in Medicine 83, 58-66 (Year: 2017).*

(Continued)

*Primary Examiner* — Ping Y Hsieh
*Assistant Examiner* — Xiao Liu
(74) *Attorney, Agent, or Firm* — McCoy Russell LLP

(57) ABSTRACT

Various methods and systems are provided for determining and characterizing features of an anatomical structure from a medical image. In one example, a method comprises acquiring a plurality of medical images over time during an exam, registering the segmented anatomical structure between the plurality of medical images, segmenting an anatomical structure in a one of the plurality of medical images after registering the plurality of medical images, creating and characterizing a reference region of interest (ROI) in each of the plurality of medical images, determining characteristics of the anatomical structure by tracking pixel values of the segmented and registered anatomical structure over time, and outputting the determined characteristics on a display device.

17 Claims, 10 Drawing Sheets

(51) Int. Cl.
| | |
|---|---|
| *G06T 7/38* | (2017.01) |
| *G06T 7/11* | (2017.01) |
| *G06T 7/174* | (2017.01) |
| *G06N 20/00* | (2019.01) |
| *G06K 9/62* | (2006.01) |
| *G06N 3/08* | (2006.01) |
| *G06T 7/00* | (2017.01) |

(52) U.S. Cl.
CPC .......... *G06N 20/00* (2019.01); *G06T 7/0014* (2013.01); *G06T 7/11* (2017.01); *G06T 7/174* (2017.01); *G06T 7/38* (2017.01); *G06T 2207/10081* (2013.01); *G06T 2207/20076* (2013.01); *G06T 2207/20081* (2013.01); *G06T 2207/20084* (2013.01); *G06T 2207/30056* (2013.01); *G06T 2207/30096* (2013.01)

(58) Field of Classification Search
CPC . G06T 2207/20076; G06T 2207/20081; G06T 2207/20084; G06T 2207/30056; G06T 2207/30096; G06N 20/00; G06N 3/084; G06K 9/6202; G06K 9/6268
See application file for complete search history.

(56) References Cited

U.S. PATENT DOCUMENTS

| | | | |
|---|---|---|---|
| 2009/0097727 A1* | 4/2009 | Jolly | A61B 6/466 382/131 |
| 2011/0158491 A1 | 6/2011 | Markova et al. | |
| 2013/0004044 A1* | 1/2013 | Ross | G06T 7/136 382/131 |
| 2017/0200266 A1 | 7/2017 | Podilchuk et al. | |
| 2020/0085382 A1* | 3/2020 | Taerum | G06T 7/30 |
| 2020/0242776 A1* | 7/2020 | Nagata | G06T 7/162 |
| 2020/0272864 A1* | 8/2020 | Faust | G06K 9/3233 |

OTHER PUBLICATIONS

Hinrichs, J. et al., "Parametric response mapping of collrast-enhanced biphasic CT for evaluating tumour viability of hepatocellular carcinoma after TACE," European Radiology, vol. 26, No. 10, Oct. 2016, Available Online Jan. 14, 2016, 10 pages.

Kim, Y. et al., "Computer-Aided Diagnosis Program for Classifying the Risk of Hepatocellular Carcinoma on MR Images Following Liver Imaging Reporting and Data System (LI-RADS)," Journal of Magnetic Resonance Imaging, vol. 47, No. 3, Mar. 2018, Available Online May 26, 2017, 13 pages.

Okamoto, S. et al., "Detection of Hepatocellular Carcinoma in CT Images Using Deep Learning," Proceedings of the 4th World Congress on Electrical Engineering and Computer Systems and Sciences (EECSS'18), Aug. 21, 2018, Madrid, Spain, 7 pages.

Wang, C. et al., "A probabilistic approach for interpretable deep learning in liver cancer diagnosis," Proceedings of the SPIE10950 Medical Imaging 2019: Computer-Aided Diagnosis Conference, Mar. 13, 2019, San Diego, California, 10 pages.

Peng, J. et al., "Residual convolutional neural network for predicting response of transarterial chemoembolization in hepatocellular carcinoma from CT imaging," European Radiology, vol. 30, vol. 1, Jan. 2020, Available Online Jul. 22, 2019, 12 pages.

Lee, J. et al., "Automatic detection method of hepatocellular carcinomas using the non-rigid registration method of multi-phase liver CT images," Journal of X-ray science and technology, vol. 23, No. 3, Jun. 2015, 14 pages.

Zheng, Y. et al., "Feature Learning Based Random Walk for Liver Segmentation," PLoS One, vol. 11, No. 11, Nov. 15, 2016, 17 pages.

Vivanti, R. et al., "Automatic detection of new tumors and tumor burden evaluation in longitudinal liver CT scan studies," International Journal of Computer Assisted Radiology and Surgery, vol. 12, No. 11, Nov. 2017, Available Online Aug. 30, 2017, 13 pages.

Lee, G. et al., "Automatic hepatocellular carcinoma lesion detection with dynamic enhancement characteristic from multi-phase CT images," Proceedings of the 2019 Joint International Workshop on Advanced Image Technology (IWAIT) and International Forum on Medical Imaging in Asia (IFMIA), Singapore, Singapore, Mar. 27, 2019, 6 pages.

Erkan, B. et al., "Non-invasive diagnostic criteria of hepatocellular carcinoma: Comparison of diagnostic accuracy of updated LI-RADS with clinical practice guidelines of OPTN-UNOS, AASLD, NCCN, EASL-EORTC, and KLSCG-NCC," PLoS One, vol. 14, No. 12, Dec. 10, 2019, 15 pages.

European Patent Office, Extended European Search Report Issued in Application No. 21150446.9, dated Jun. 25, 2021, Germany, 13 pages.

* cited by examiner

METHODS AND SYSTEMS FOR CHARACTERIZING ANATOMICAL FEATURES IN MEDICAL IMAGES

TECHNICAL FIELD

Embodiments of the subject matter disclosed herein relate to medical imaging systems, and more particularly, to image feature analyses using deep neural networks.

BACKGROUND

Liver cancer is a prominent cause of cancer-related deaths worldwide, and hepatocellular carcinoma (HCC) is the most common type of liver cancer. Early tumor detection and evaluation may favorably affect patient prognosis. As one example, a contrast-enhanced computed tomography (CT) scan may be used as a non-invasive method to assess liver tissue in patients at risk of HCC. The CT scan uses differential transmission of x-rays through a target volume (which includes the liver when the patient is evaluated for HCC) to acquire image data and to construct tomographic images (e.g., three-dimensional representations of the interior of the human body). The Liver Imaging Reporting and Data System, or LI-RADS, provides criteria for interpreting and reporting the resulting images from the CT scan.

In some examples, follow-up scans may be performed post-treatment to evaluate an effectiveness of the treatment. For example, during the analysis of follow-up scans, a user/physician may compare grayscale values of relevant tissue regions to assess pre- and post-treatment differences. If an identified lesion shows significantly reduced viable tissue in a follow-up scan after a therapy course, this may indicate a positive response to the therapy, for example. Otherwise, no response or progressive disease may be indicated.

SUMMARY

In one embodiment, a method comprises acquiring a plurality of medical images over time during an exam, registering the plurality of medical images, segmenting an anatomical structure in one of the plurality of medical images after registering the plurality of medical images, creating and characterizing a reference region of interest (ROI) in each of the plurality of medical images, determining characteristics of the anatomical structure by tracking pixel values of the segmented anatomical structure over time, and outputting the determined characteristics on a display device. In this way, the anatomical structure may be quickly and accurately characterized.

The above advantages and other advantages and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
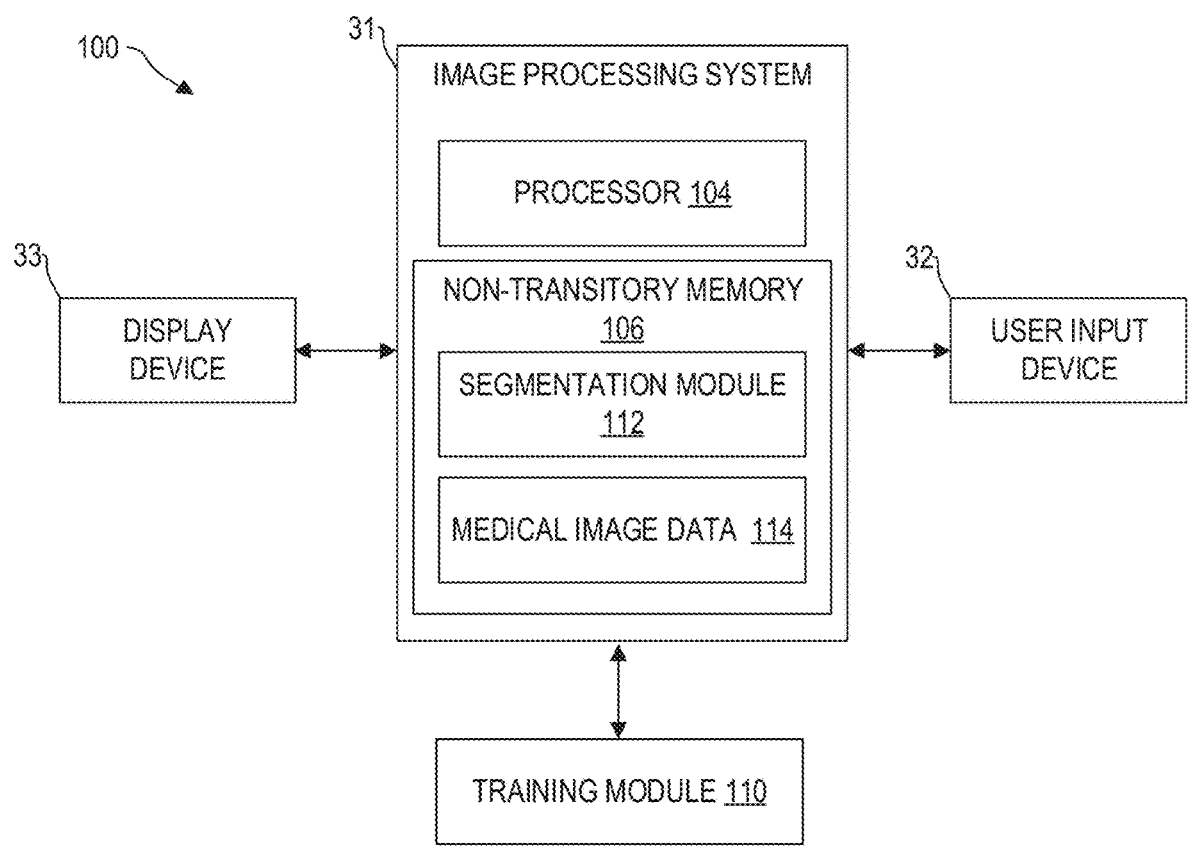
FIG. 1 is a schematic diagram illustrating an image processing system for segmenting and tracking anatomical features across multiple images, according to embodiment.

The following description relates to systems and methods for characterizing and tracking changes to an anatomical structure, such as a cancerous lesion. In particular, systems and method are provided for determining characteristics of a hepatocellular carcinoma (HCC) lesion based on images acquired during a multi-phasic computed tomography (CT) exam. One such multi-phasic CT exam includes a CT scan of the patient with four sequential acquisitions: acquisition of a non-contrasted (or unenhanced) image prior to injection of a contrast agent, and acquisition of additional images after injection of the contrast agent corresponding to arterial, portal, and delayed phases of the contrast agent uptake and wash-out. In some examples, a physician may rely on the images obtained during the multi-phasic CT exam to identify potentially cancerous tissue and to categorize the lesion according to a standardized scoring process (e.g., the Liver Imaging Reporting and Data System, or LI-RADS), which gives an indication of its malignancy. In other examples, the physician may use the images obtained during the multi-phasic CT exam to track changes to a known lesion over time in order to evaluate a response to a treatment and further develop a treatment strategy. However, accurate processing of the liver images obtained during the multi-phasic CT remains challenging due to complex liver backgrounds, breathing movements, ambiguous tumor boundaries, heterogeneous appearances, and highly varied shapes of the tumor and the liver. Further, the LI-RADS scoring and post-treatment assessment are both complex and subjective to the physician performing the analysis, which may lead to variability and/or misdiagnosis.

Thus, according to embodiments disclosed herein, a workflow including image processing and deep learning methods is provided to increase the efficiency and accuracy of HCC tumor detection and characterization. The workflow may be used to identify characteristics of a naïve HCC lesion (e.g., prior to treatment) in order to categorize the lesion according to LI-RADS features and/or to evaluate changes in the HCC lesion over time, such as following treatment. Such follow-up studies can indicate, for example, a physiological response to a certain medical treatment and may help in determining a treatment plan. For example, the workflow may segment the liver and the lesion within the liver in each image acquired during the multi-phasic CT exam, register the segmented liver and lesion between the images, and determine pre-treatment or post-treatment characteristics of the lesion by sub-segmenting the tissue within the lesion, which may be output to the physician for evaluation. By using an automated workflow that combines image processing and deep learning methods to characterize cancerous lesions, both inter- and intra-physician variability may be reduced. Further, misdiagnosis may be reduced by reducing an amount of subjectivity in the tumor assessment. In this way, an accuracy of a cancer diagnosis and prognosis may be increased while reducing a mental burden on the physician.

Figure 3:
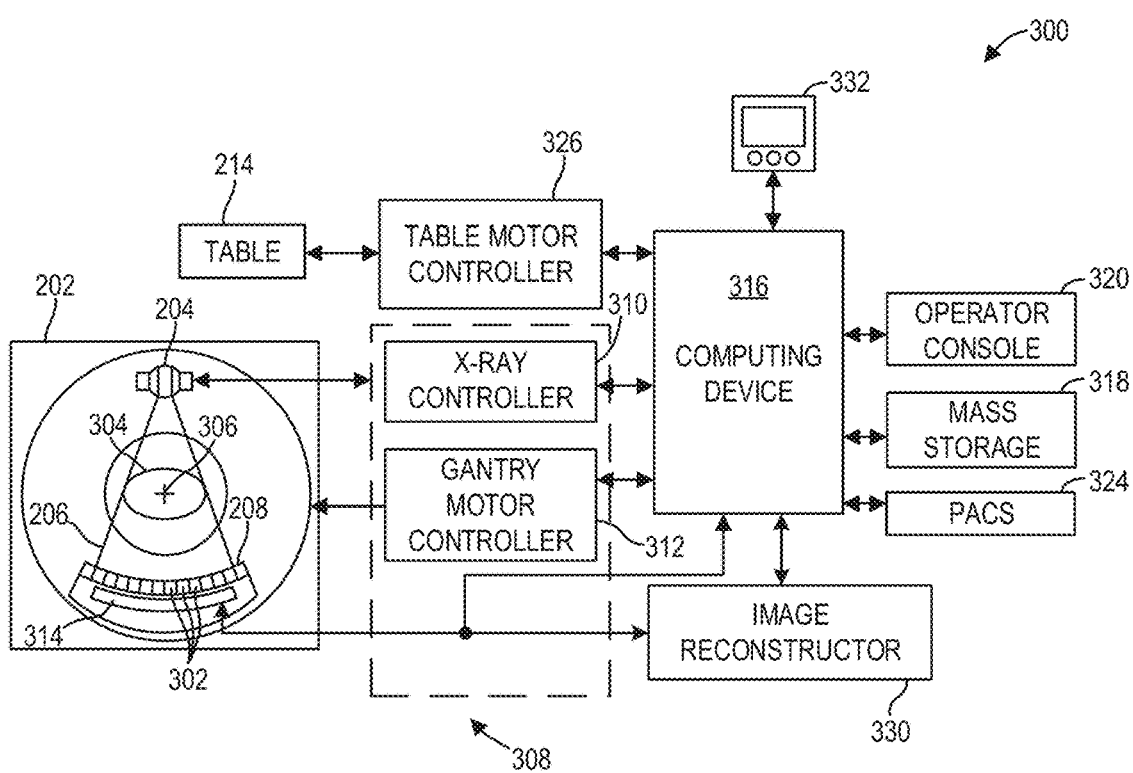
FIG. 3 shows a block schematic diagram of an exemplary imaging system, according to an embodiment.
Figure 4:
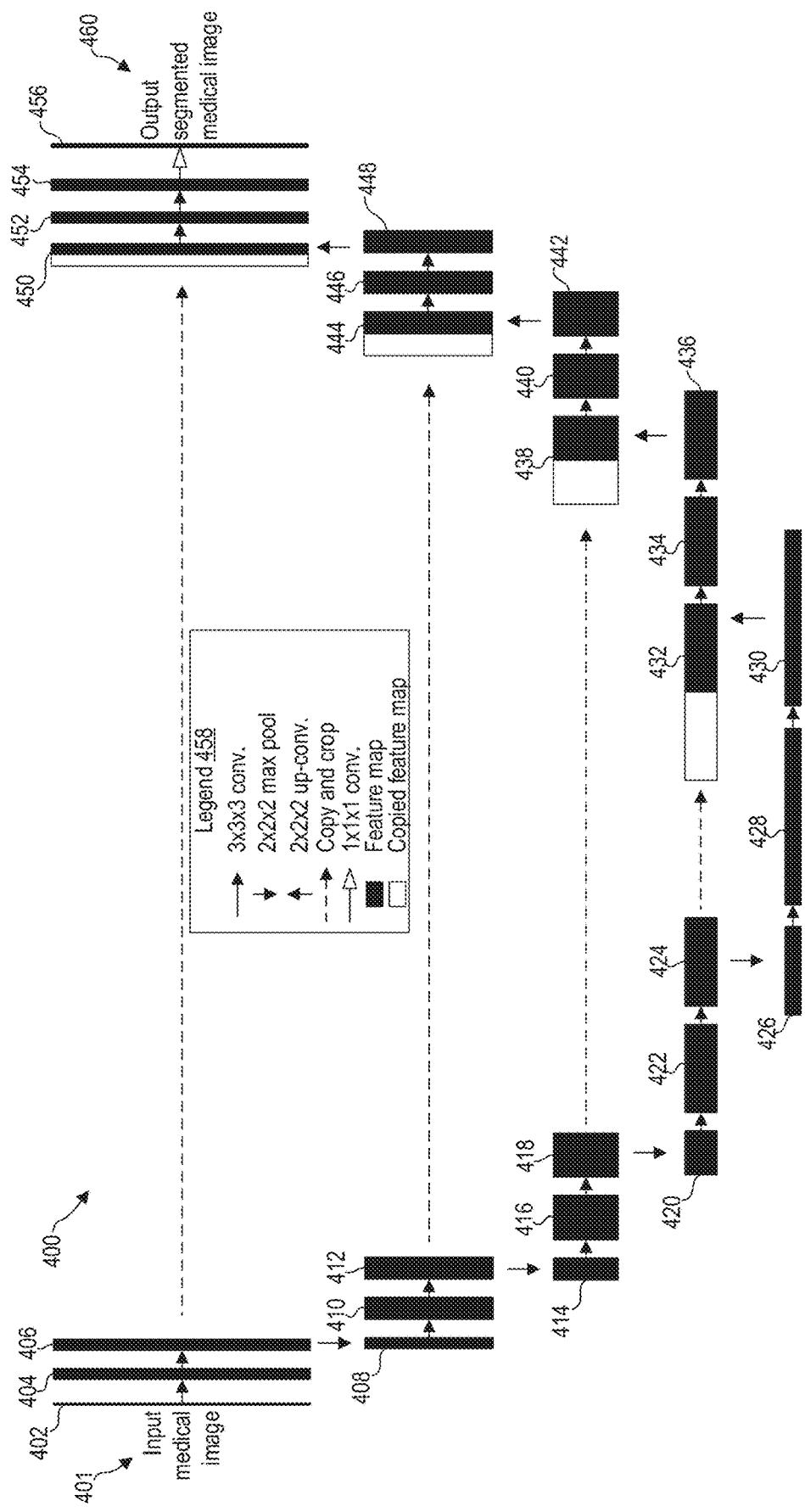
FIG. 4 is a schematic diagram illustrating an architecture of a deep learning network that may be used in the system of FIG. 1, according to an embodiment.
Figure 6:
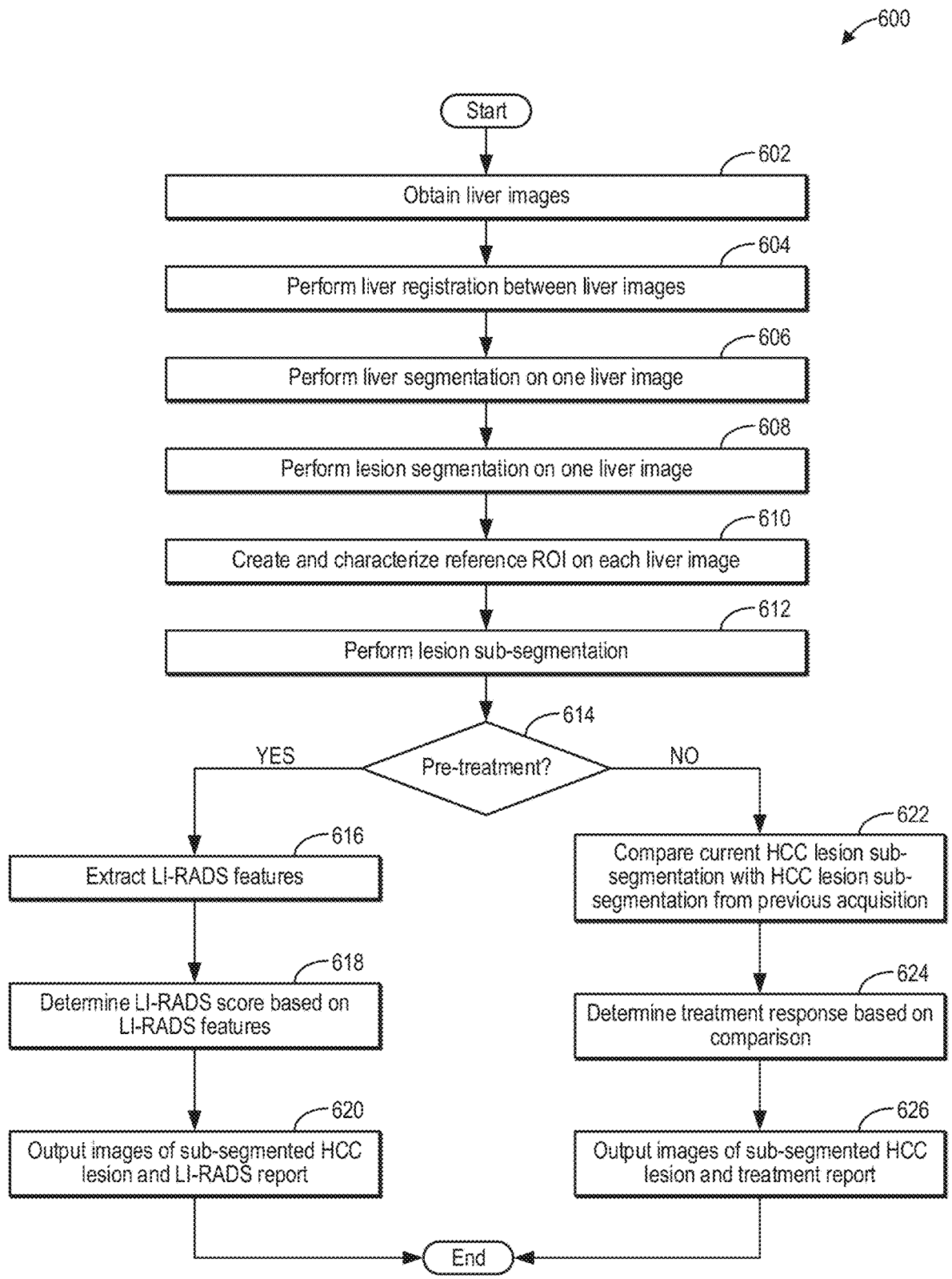
FIG. 6 is a high-level flowchart illustrating a method for analyzing and characterizing hepatocellular carcinoma (HCC) lesions in a multi-phasic exam, according to an embodiment.
Figure 7:
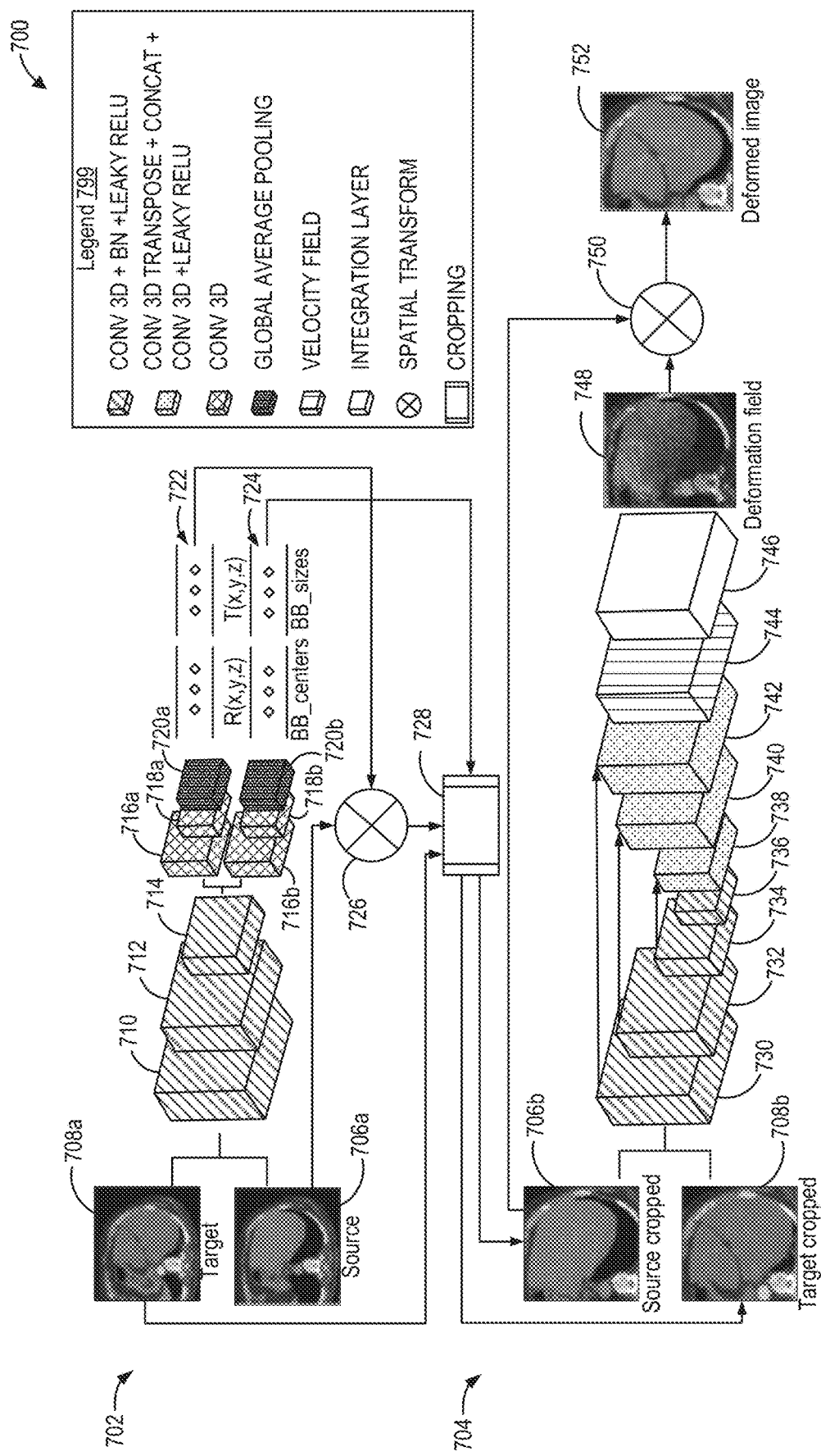
FIG. 7 shows a schematic diagram illustrating an example deep learning approach for aligning images from a multi-phasic exam, according to an embodiment.
Figure 8:
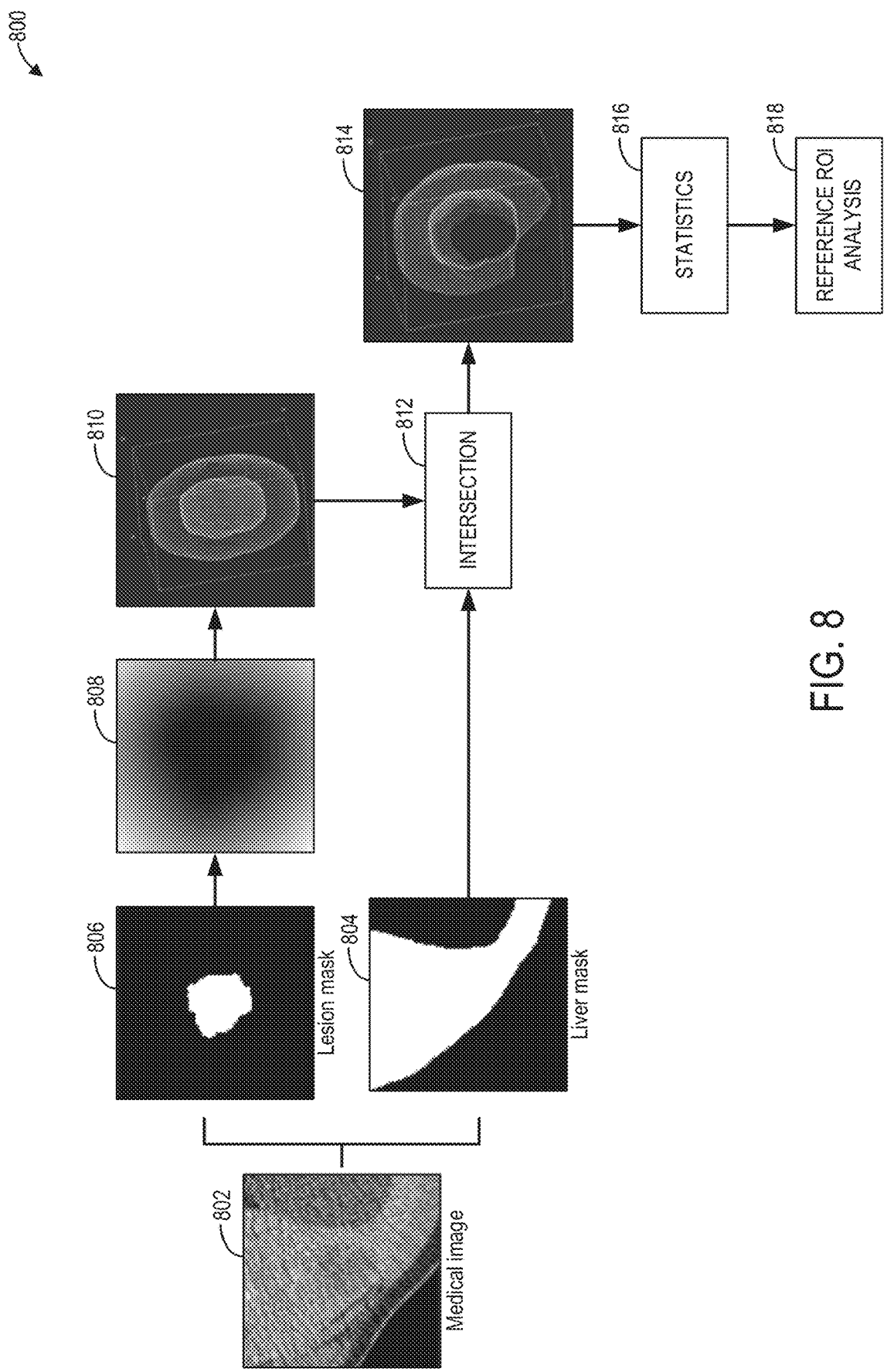
FIG. 8 shows a block schematic diagram of a workflow for creating and analyzing a reference region of interest (ROI)
Figure 9:
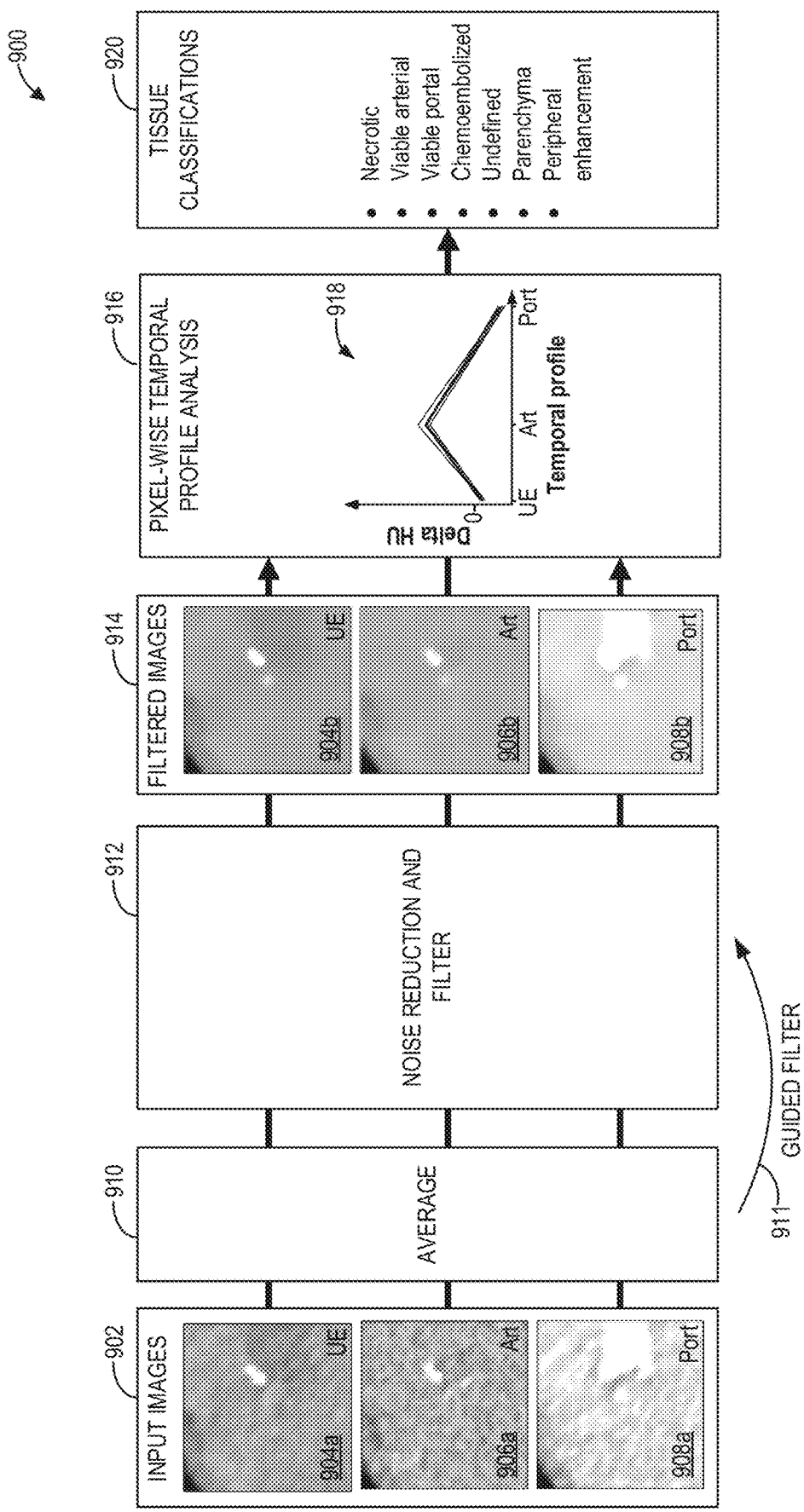
FIG. 9 shows a block schematic diagram of a workflow for performing HCC lesion sub-segmentation and characterization, according to an embodiment.
Figure 10:
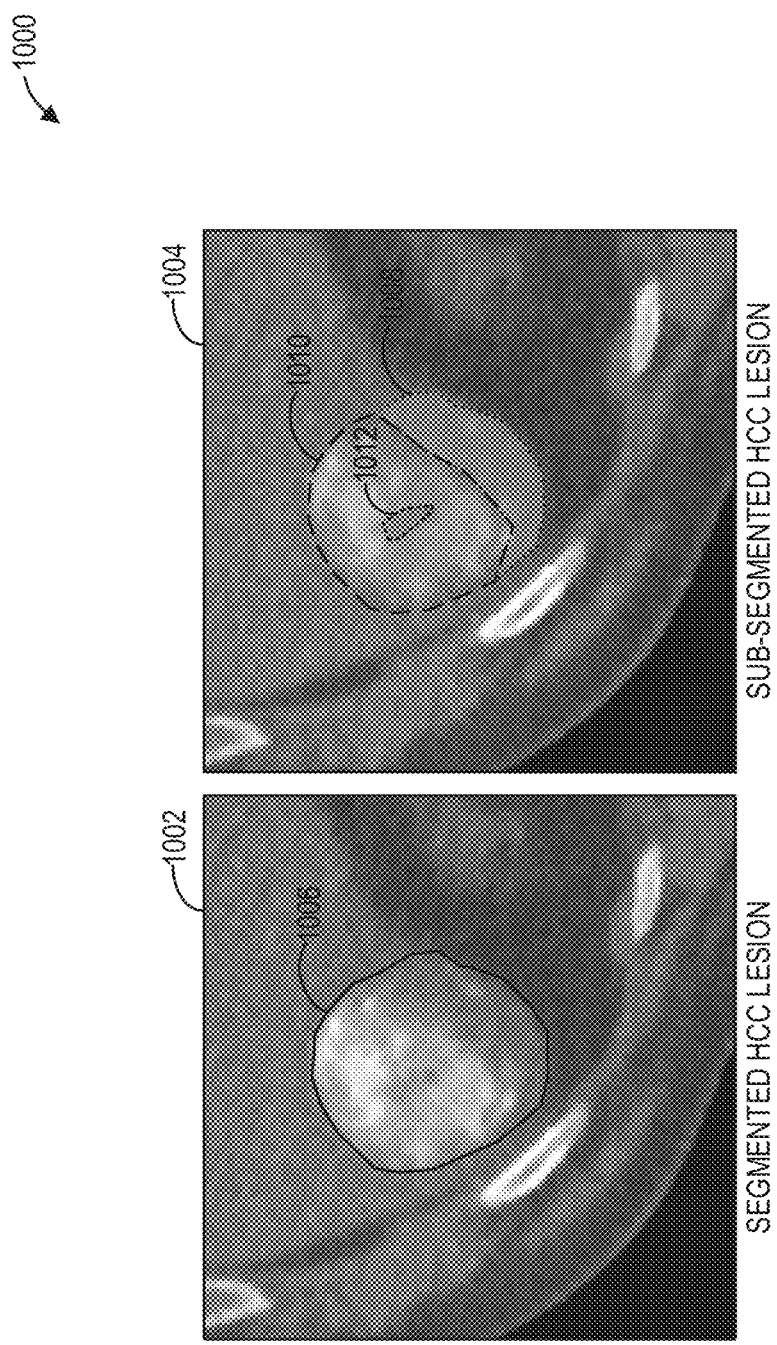
FIG. 10 shows an example of lesion sub-segmentation and characterization, according to an embodiment.
Figure 11:
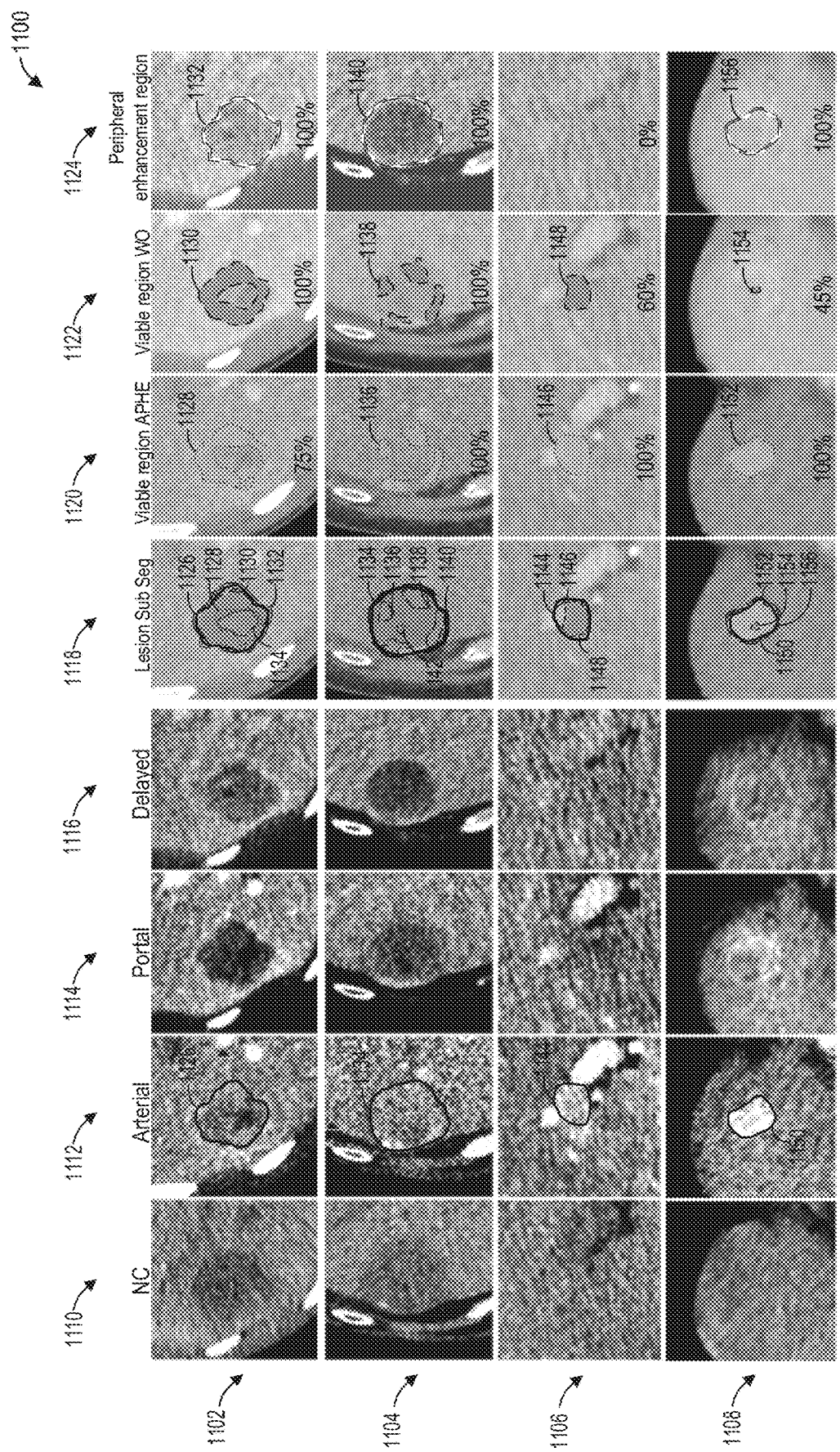
FIG. 11 shows an example of feature extraction from liver images obtained during a multi-phasic exam, according to an embodiment.

FIG. 1 shows an exemplary image processing system for implementing a deep learning model, which may be the deep learning model shown in FIG. 4. The deep learning model may include a plurality of neural network models, each trained with a training set such as according to the example method of FIG. 5. An imaging system, such as the CT imaging system shown in FIGS. 2 and 3, may be used to generate images that are analyzed by the image processing system of FIG. 1. FIG. 6 shows an example method of a workflow for determining and/or tracking characteristics of a lesion using the example deep learning model of FIG. 4. In particular, the method of FIG. 6 may analyze contrast agent dynamics across multiple exam phases to segment the liver from other anatomical features, segment the lesion from other liver tissues, and sub-segment the lesion based on the various tissues found therein. In order to use images from multiple exam phases, FIG. 7 shows an example deep learning approach for image alignment that may be used in the method of FIG. 6. FIG. 8 schematically shows a workflow that may be used to determine and analyze a reference region of interest (ROI) within healthy liver tissue surrounding the lesion. FIG. 9 schematically shows a workflow that may be used in the method of FIG. 6 to classify the sub-segmented lesion tissues. FIG. 10 shows example frames of a sub-segmented lesion, and FIG. 11 shows example frames that may be used for extracting features of the lesion for LI-RADS scoring.

Referring to FIG. 1, an example medical image processing system 100 is shown. In some embodiments, the medical image processing system 100 is incorporated into a medical imaging system, such as a magnetic resonance imaging (MRI) system, a CT system, a single-photon emission computed tomography (SPECT) system, etc. In some embodiments, at least a portion of the medical image processing system 100 is disposed at a device (e.g., an edge device or server) communicably coupled to the medical imaging system via wired and/or wireless connections. In some embodiments, the medical image processing system 100 is disposed at a separate device (e.g., a workstation) that can receive images from the medical imaging system or from a storage device that stores the images generated by the medical imaging system. The medical image processing system 100 may comprise an image processing system 31, a user input device 32, and a display device 33. For example, the image processing system 31 may be operatively/communicatively coupled to the user input device 32 and the display device 33.

The image processing system 31 includes a processor 104 configured to execute machine readable instructions stored in non-transitory memory 106. The processor 104 may be single core or multi-core, and the programs executed by processor 104 may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration. In some embodiments, the processor 104 may include other electronic components capable of carrying out processing functions, such as a digital signal processor, a field-programmable gate array (FPGA), or a graphic board. In some embodiments, the processor 104 may include multiple electronic components capable of carrying out processing functions. For example, the processor 104 may include two or more electronic components selected from a plurality of possible electronic components, including a central processor, a digital signal processor, a field-programmable gate array, and a graphics board. In still further embodiments, the processor 104 may be configured as a graphical processing unit (GPU), including parallel computing architecture and parallel processing capabilities.

The non-transitory memory 106 may store a segmentation module 112 and medical image data 114. The segmentation module 112 may include one or more machine learning models, such as deep learning networks, comprising a plurality of weights and biases, activation functions, loss functions, gradient descent algorithms, and instructions for implementing the one or more deep neural networks to process input medical images. For example, segmentation module 112 may store instructions for implementing a neural network, such as a convolutional neural network (CNN) 400 shown in FIG. 4 and described below. Segmentation module 112 may include trained and/or untrained neural networks and may further include training routines, or parameters (e.g., weights and biases), associated with one or more neural network models stored therein.

Image processing system 31 may be communicatively coupled to a training module 110, which includes instructions for training one or more of the machine learning models stored in the segmentation module 112. Training module 110 may include instructions that, when executed by a processor, cause the processor to conduct the steps of method 500 of FIG. 5, discussed in more detail below. In one example, training module 110 includes instructions for receiving training data sets from the medical image data 114, which comprise sets of medical images, associated ground truth labels/images, and associated model outputs for use in training one or more of the machine learning models stored in segmentation module 112. Training module 110 may receive medical images, associated ground truth labels/images, and associated model outputs for use in training the one or more machine learning models from sources other than the medical image data 114, such as other image processing systems, the cloud, etc. In some embodiments, one or more aspects of training module 110 may include remotely-accessible networked storage devices configured in a cloud computing configuration. Further, in some embodiments, the training model 110 is included in the non-transitory memory 106. Additionally or alternatively, in some embodiments, the training model 110 may be used to generate the segmentation module 112 offline and remote from the image processing system 100. In such embodiments, the training module 110 may not be included in the image processing system 100 but may generate data stored in the image processing system 100.

The non-transitory memory 106 further stores the medical image data 114. The medical image data 114 includes for example, functional imaging images captured by a functional imaging modality, such as SPECT and PET systems, anatomical images captured by an MRI system or a CT system, etc. For example, the medical image data 114 may include initial and follow-up medical scan images stored in the non-transitory memory 106. As one example, the medical image data 114 may include a series of CT images acquired during a multi-phase contrast-enhanced exam of a patient's liver.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices in a cloud computing configuration.

Image processing system 100 may further include user input device 32. User input device 32 may comprise one or more of a touchscreen, a keyboard, a mouse, a trackpad, a motion sensing camera, or other device configured to enable a user to interact with and manipulate data within image processing system 31. As an example, user input device 32 may enable a user to analyze and rank imaged structures.

Display device 33 may include one or more display devices utilizing any type of display technology. In some embodiments, display device 33 may comprise a computer monitor and may display unprocessed images, processed images, parametric maps, and/or exam reports. Display device 33 may be combined with processor 104, non-transitory memory 106, and/or user input device 32 in a shared enclosure or may be a peripheral display device. Display device 33 may include a monitor, a touchscreen, a projector, or another type of display device, which may enable a user to view medical images and/or interact with various data stored in the non-transitory memory 106.

It should be understood that image processing system 100 shown in FIG. 1 is one non-limiting embodiment of an image processing system, and other imaging processing systems may include more, fewer, or different components without parting from the scope of this disclosure.

Figure 2:
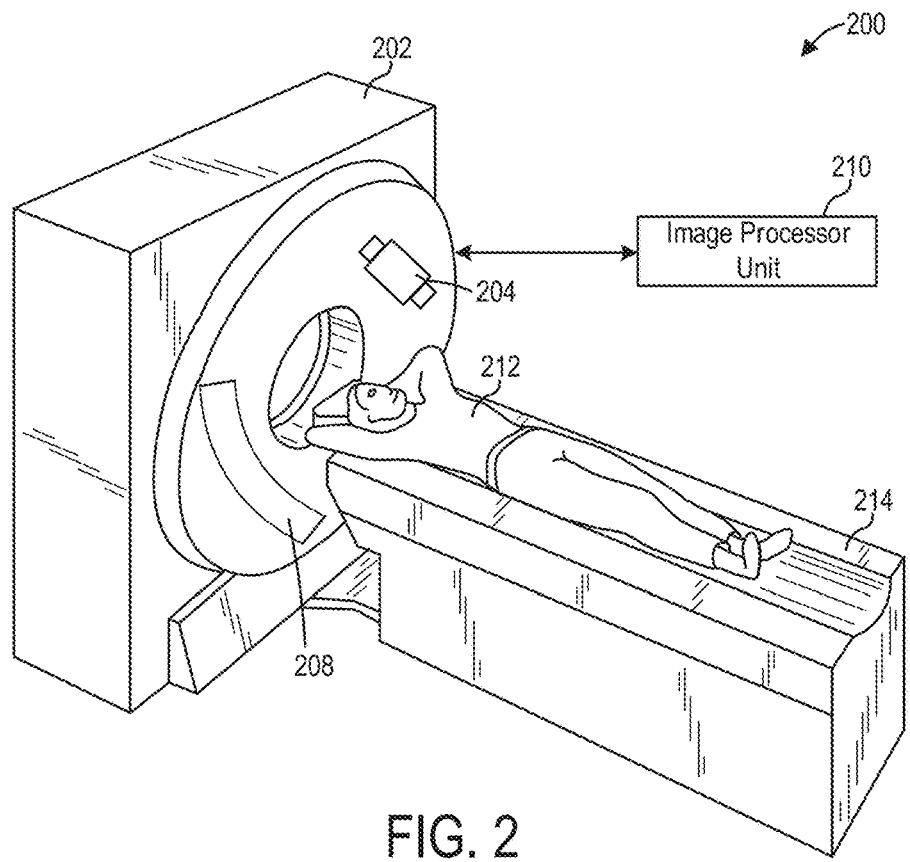
FIG. 2 shows a pictorial view of an imaging system that may utilize an image processing system, such as image processing system of FIG. 1, according to an embodiment.

FIG. 2 illustrates an exemplary CT system 200 configured for CT imaging. Particularly, the CT system 200 is configured to image a subject 212, such as a patient, an inanimate object, one or more manufactured parts, and/or foreign objects such as dental implants, stents, and/or contrast agents present within the body. The CT system 200 may be used to generate medical images processed by the image processing system 100 of FIG. 1, for example. In one embodiment, the CT system 200 includes a gantry 202, which, in turn, may further include at least one x-ray source 204 configured to project a beam of x-ray radiation 206 (see FIG. 3) for use in imaging the subject 212 laying on a table 214. Specifically, the x-ray source 204 is configured to project the x-ray radiation 206 toward a detector array 208 positioned on the opposite side of the gantry 202. Although FIG. 2 depicts only a single x-ray source 204, in certain embodiments, multiple x-ray sources and detectors may be employed to project a plurality of x-ray radiation beams 206 for acquiring projection data at different energy levels corresponding to the patient. In some embodiments, the x-ray source 204 may enable dual-energy gemstone spectral imaging (GSI) by rapid peak kilovoltage (kVp) switching. In some embodiments, the x-ray detector employed is a photon-counting detector, which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 200 further includes an image processor unit 210 configured to reconstruct images of a target volume of the subject 212 using an iterative or analytic image reconstruction method. For example, the image processor unit 210 may use an analytic image reconstruction approach such as filtered back projection (FBP) to reconstruct images of a target volume of the patient. As another example, the image processor unit 210 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 212. As described further herein, in some examples, the image processor unit 210 may use both an analytic image reconstruction approach such as FBP in addition to an iterative image reconstruction approach. In some examples, the image processor unit 210 may be included as a part of or communicatively coupled to the image processing system 31 of FIG. 1.

In some configurations of the CT system 200, the x-ray source 204 projects a cone-shaped x-ray radiation beam, which is collimated to lie within an X-Y-Z plane of a Cartesian coordinate system and generally referred to as an "imaging plane." The x-ray radiation beam 206 passes through an object being imaged, such as the patient 212. The x-ray radiation beam, after being attenuated by the object, impinges upon an array of detector elements at the detector array 208. The intensity of the attenuated x-ray radiation beam received at the detector array 208 is dependent upon the attenuation of the x-ray radiation beam by the object. Each detector element of the array produces a separate electrical signal that is a measurement of the x-ray beam attenuation at the detector location. The attenuation measurements from all the detector elements are acquired separately to produce a transmission profile.

In some configurations of the CT system 200, the x-ray source 204 and the detector array 208 are rotated with the gantry 202 within the imaging plane and around the object to be imaged such that an angle at which the x-ray radiation beam 206 intersects the object constantly changes. A group of x-ray radiation attenuation measurements, e.g., projection data, from the detector array 208 at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused (e.g., hybrid) embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to as the filtered back projection technique. Transmission and emission tomography reconstruction techniques also include statistical iterative methods such as the maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," (HU), which are used to control the brightness (or intensity) of a corresponding pixel on a display device.

To reduce the total scan time, a "helical" scan may be performed. To perform the helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 3 illustrates an exemplary imaging system 300 similar to the CT system 200 of FIG. 2. In accordance with aspects of the present disclosure, the imaging system 300 is configured for imaging a subject 304 (e.g., the subject 212 of FIG. 2). In one embodiment, the imaging system 300 includes the detector array 208 (see FIG. 2). The detector array 208 further includes a plurality of detector elements 302 that together sense the x-ray radiation beam 206 (see FIG. 3) that pass through the subject 304 (such as a patient) to acquire corresponding projection data. Accordingly, in one embodiment, the detector array 208 is fabricated in a multi-slice configuration including the plurality of rows of cells or detector elements 302. In such a configuration, one or more additional rows of the detector elements 302 are arranged in a parallel configuration for acquiring the projection data.

In certain embodiments, the imaging system 300 is configured to traverse different angular positions around the subject 304 for acquiring desired projection data. Accordingly, the gantry 202 and the components mounted thereon may be configured to rotate about a center of rotation 306 for acquiring the projection data, for example, at different energy levels. Alternatively, in embodiments where a projection angle relative to the subject 304 varies as a function of time, the mounted components may be configured to move along a general curve rather than along a segment of a circle.

As the x-ray source 204 and the detector array 208 rotate, the detector array 208 collects data of the attenuated x-ray beams. The data collected by the detector array 208 undergoes pre-processing and calibration to condition the data to represent the line integrals of the attenuation coefficients of the scanned subject 304. The processed data are commonly called projections. In some examples, the individual detectors or detector elements 302 of the detector array 208 may include photon-counting detectors that register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 300 reveals internal features of the subject 304, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 300 includes a control mechanism 308 to control movement of the components such as rotation of the gantry 202 and the operation of the x-ray source 204. In certain embodiments, the control mechanism 308 further includes an x-ray controller 310 configured to provide power and timing signals to the x-ray source 204. Additionally, the control mechanism 308 includes a gantry motor controller 312 configured to control a rotational speed and/or position of the gantry 202 based on imaging requirements.

In certain embodiments, the control mechanism 308 further includes a data acquisition system (DAS) 314 configured to sample analog data received from the detector elements 302 and convert the analog data to digital signals for subsequent processing. The DAS 314 may be further configured to selectively aggregate analog data from a subset of the detector elements 302 into so-called macro-detectors, as described further herein. The data sampled and digitized by the DAS 314 is transmitted to a computer or computing device 316. In one example, the computing device 316 stores the data in a storage device or mass storage 318. The storage device 318, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 316 provides commands and parameters to one or more of the DAS 314, the x-ray controller 310, and the gantry motor controller 312 for controlling system operations such as data acquisition and/or processing. In certain embodiments, the computing device 316 controls system operations based on operator input. The computing device 316 receives the operator input, for example, including commands and/or scanning parameters via an operator console 320 operatively coupled to the computing device 316. The operator console 320 may include a keyboard (not shown) or a touchscreen, for example, to allow the operator to specify the commands and/or scanning parameters.

Although FIG. 3 illustrates only one operator console 320, more than one operator console may be coupled to the imaging system 300, for example, for inputting or outputting system parameters, requesting examinations, plotting data, and/or viewing images. Further, in certain embodiments, the imaging system 300 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc. For example, imaging system 300 may be coupled to image processing system 100 of FIG. 1.

In one embodiment, for example, the imaging system 300 either includes, or is coupled to, a picture archiving and communications system (PACS) 324. In an exemplary implementation, the PACS 324 is further coupled to a remote system such as a radiology department information system, hospital information system, and/or to an internal or external network (not shown) to allow operators at different locations to supply commands and parameters and/or gain access to the image data.

The computing device 316 uses the operator-supplied and/or system-defined commands and parameters to operate a table motor controller 326, which in turn, may control the table 214, which may be a motorized table. Specifically, the table motor controller 326 may move the table 214 for appropriately positioning the subject 304 in the gantry 202 for acquiring projection data corresponding to the target volume of the subject 304.

As previously noted, the DAS 314 samples and digitizes the projection data acquired by the detector elements 302. Subsequently, an image reconstructor 330 uses the sampled and digitized x-ray data to perform high-speed reconstruction. Although FIG. 3 illustrates the image reconstructor 330 as a separate entity, in certain embodiments, the image reconstructor 330 may form part of the computing device 316. Alternatively, the image reconstructor 330 may be absent from the imaging system 300, and instead the computing device 316 may perform one or more functions of the image reconstructor 330. Moreover, the image reconstructor 330 may be located locally or remotely, and may be operatively connected to the imaging system 300 using a wired or wireless network. Particularly, one exemplary embodiment may use computing resources in a "cloud" network cluster for the image reconstructor 330. Further, in some examples, the image reconstructor 330 is included as a part of image processor unit 210 of FIG. 2.

In one embodiment, the image reconstructor 330 stores the images reconstructed in the storage device 318. Alternatively, the image reconstructor 330 may transmit the reconstructed images to the computing device 316 for generating useful patient information for diagnosis and evaluation. In certain embodiments, the computing device 316 may transmit the reconstructed images and/or the patient information to a display or display device 332 communicatively coupled to the computing device 316 and/or the image reconstructor 330. In one embodiment, the display 332 allows the operator to evaluate the imaged anatomy. The display 332 may also allow the operator to select a volume of interest (VOI) and/or request patient information, for example, via a graphical user interface (GUI) for a subsequent scan or processing.

In some embodiments, the reconstructed images may be transmitted from the computing device 316 or the image reconstructor 330 to the storage device 318 for short-term or long-term storage. Further, in some embodiments, the computing device 316 may be or may be operationally coupled to the processor 104 of FIG. 1. As such, raw data and/or images reconstructed from data acquired by the imaging system 300 may be transmitted to the image processing system 100 (see FIG. 1) for further processing and analysis. Further, the various methods and processes described further herein (such as the method described below with reference to FIG. 6) may be stored as executable instructions in non-transitory memory on a computing device (or controller). At least some of the instructions may be stored in non-transitory memory in imaging system 300. In one embodiment, the image reconstructor 330 may include such executable instructions in non-transitory memory to reconstruct an image from scanning data. In another embodiment, computing device 316 may include the instructions in non-transitory memory, and may apply the methods described herein, at least in part, to a reconstructed image after receiving the reconstructed image from image reconstructor 330. In yet another embodiment, the methods and processes described herein may be distributed across the image reconstructor 330 and the computing device 316. Additionally or alternatively, the methods and processes described herein may be distributed across imaging system 300 (e.g., in the image reconstructor 330 and/or the computing device 316) and the medical image processing system 100 of FIG. 1 (e.g., in the processor 104 and/or the non-transitory memory 106).

Turning to FIG. 4, an example convolutional neural network (CNN) architecture 400 for segmenting a medical image of an anatomical feature is shown. For example, CNN 400 may segment an anatomical feature of interest from other anatomical features in the image. For example, the segmentation may define a boundary between the anatomical feature of interest and other tissues, organs, and structures. FIG. 4 will be described using the liver as the anatomical feature of interest, with the CNN architecture 400 used to segment the liver from other anatomical features. However, it may be understood that in other examples, the CNN architecture 400 may be applied to segmenting other anatomical features. CNN 400 represents one example of a machine learning model according to the present disclosure, wherein the parameters of CNN 400 may be learned using training data produced according to one or more methods disclosed herein, such as the method of FIG. 5 described below.

The CNN architecture 400 represents a U-net architecture, which may be divided into an encoder portion (descending portion, elements 402-430) and a decoder portion (ascending portion, elements 432-456). The CNN architecture 400 is configured to receive medical images, which may be, for example, magnetic resonance (MR) images, computed tomography (CT) images, SPECT images, or the like. In one embodiment, the CNN architecture 400 is configured to receive data from a CT image, such as an input medical image 401, comprising a plurality of pixels/voxels and map the input image data to a segmented image of the liver, such as an output segmented medical image 460, based on an output of an acquisition parameter transform. CNN architecture 400 will be described as a 3D network, although 2D networks may include a similar architecture. Thus, the input medical image 401 is an input 3D volume including a plurality of voxels.

The CNN architecture 400 comprises a series of mappings, which extend from an input image tile 402 (which may be received by an input layer from the input medical image 401) through a plurality of feature maps and finally to the output segmented medical image 460. The output segmented medical image 460, which is an output 3D volume, may be produced based on output from an output layer 456.

The various elements comprising the CNN architecture 400 are labeled in a legend 458. As indicated by the legend 458, the CNN architecture 400 includes a plurality of feature maps (and/or copied feature maps) connected by one or more operations indicated by arrows. The arrows/operations receive input from either an external file or a previous feature map and transform/map the received input to produce a next feature map. Each feature map may comprise a plurality of neurons. In some embodiments, each neuron may receive input from a subset of neurons of a previous layer/feature map and may compute a single output based on the received inputs. The output may be propagated/mapped to a subset or all of the neurons in a next layer/feature map. A feature map may be described using spatial dimensions, such as length, width, and depth, wherein the dimensions refer to the number of neurons comprising the feature map (e.g., how many neurons long, how many neurons wide, and how many neurons deep, a specified feature map is).

In some embodiments, the neurons of the feature maps may compute an output by performing a convolution of received inputs using a set of learned weights (each set of learned weights may herein be referred to as a filter), wherein each received input has a unique corresponding learned weight, wherein the learned weight was learned during training of the CNN.

The transformations/mappings performed between each feature map are indicated by arrows. Each distinct type of arrow corresponds to a distinct type of transformation, as indicated by the legend 458. Rightward pointing solid black arrows indicate 3×3×3 convolutions with stride of one, wherein output from a 3×3×3 grid of feature channels of an immediately preceding feature map are mapped to a single feature channel of a current feature map. Each 3×3×3 convolution may be followed by an activation function, wherein, in one embodiment, the activation function comprises a rectified linear unit (ReLU).

Downward pointing arrows indicate 2×2×2 max pooling operations, wherein the max value from a 2×2×2 grid of feature channels at a single depth is propagated from an immediately preceding feature map to a single feature channel of a current feature map, thereby resulting in an output feature map with a 8-fold reduction in spatial resolution as compared to the immediately preceding feature map.

Upward pointing arrows indicate 2×2×2 up-convolutions, which comprise mapping output from a single feature channel of an immediately preceding feature map to a 2×2×2 grid of feature channels in a current feature map, thereby increasing the spatial resolution of the immediately preceding feature map 8-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map, are equal, no cropping may be performed.

Rightward pointing arrows with hollow heads indicate a 1×1×1 convolution, in which each feature channel in an immediately preceding feature map is mapped to a single feature channel of a current feature map, or in other words, wherein a 1-to-1 mapping of feature channels between an immediately preceding feature map and a current feature map occurs. Processing at every feature map may include the above-described convolutions and deconvolutions as well as activations, where activation functions are non-linear functions that restrict the output values of the processing to a bounded range.

In addition to the operations indicated by the arrows within legend 458, CNN architecture 400 includes solid filled rectangles representing feature maps, wherein feature maps comprise a height (top to bottom length as shown in FIG. 4, which corresponds to a y spatial dimension in an x-y plane), width (not shown in FIG. 4, assumed equal in magnitude to height, and corresponds to an x spatial dimension in an x-y plane), and depth (a left-right length as shown in FIG. 4, which corresponds to the number of features within each feature channel). Likewise, CNN architecture 400 includes hollow (unfilled) rectangles, which represent copied and cropped feature maps, wherein copied feature maps comprise height (top to bottom length as shown in FIG. 4, which corresponds to a y spatial dimension in an x-y plane), width (not shown in FIG. 4, assumed equal in magnitude to height, and corresponds to an x spatial dimension in an x-y plane), and depth (a length from a left side to a right side as shown in FIG. 4, which corresponds to the number of features within each feature channel).

Starting at input image tile 402 (herein also referred to as an input layer), data corresponding to the medical image 401 is input and mapped to a first set of features. In some embodiments, the input medical image 401 is pre-processed (e.g., normalized) before being processed by the neural network. The weights/parameters of each layer of CNN 400 may be learned during a training process, wherein matched pairs of input and expected output (ground truth output) are fed to CNN 400. Parameters may be adjusted based on a gradient descent algorithm or other algorithm until the output of CNN 400 matches the expected output (the ground truth output) within a threshold degree of accuracy. The input medical image 401 may comprise a two-dimensional (2D) or three-dimensional (3D) image/map of the liver (or, in other examples, another patient anatomical region).

As indicated by the solid black rightward pointing arrow immediately to the right of input image tile 402, a 3×3×3 convolution of the feature channels of input image tile 402 is performed to produce a feature map 404. As discussed above, a 3×3×3 convolution includes mapping input from a 3×3×3 grid of feature channels to a single feature channel of a current feature map, using learned weights, wherein the learned weights are referred to as a convolution filter. Each 3×3×3 convolution in CNN architecture 400 may include a subsequent activation function, which in one embodiment includes passing the output of each 3×3×3 convolution through a ReLU. In some embodiments, activation functions other than ReLUs may be employed, such as Softplus (also referred to as SmoothReLUs), leaky ReLUs, noisy ReLUs, exponential linear units (ELUs), Tan h, Gaussian, Sin c, Bent identity, logistic functions, and other activation functions known in the art of machine learning.

As indicated by the solid black rightward pointing arrow immediately to the right of feature map 404, a 3×3×3 convolution is performed on feature map 404 to produce a feature map 406.

As indicated by the downward pointing arrow beneath feature map 406, a 2×2×2 max pooling operation is performed on feature map 406 to produce a feature map 408. Briefly, the 2×2×2 max pooling operation includes determining a max feature value from a 2×2×2 grid of feature channels of an immediately preceding feature map and setting a single feature in a single feature channel of a current feature map to the determined max feature value. Additionally, feature map 406 is copied and concatenated with output from a feature map 448 to produce a feature map 450, as indicated by the dash-tailed rightward pointing arrow immediately to the right of feature map 406.

As indicated by the solid black rightward pointing arrow immediately to the right of feature map 408, a 3×3×3 convolution with stride 1 is performed on feature map 408 to produce a feature map 410. As indicated by the solid black rightward pointing arrow immediately to the right of feature map 410, a 3×3×3 convolution with stride 1 is performed on feature map 410 to produce a feature map 412.

As indicated by the downward pointing hollow headed arrow beneath feature map 412, a 2×2×2 max pooling operation is performed on feature map 412 to produce a feature map 414, wherein feature map 414 is of one fourth the spatial resolution of feature map 412. Additionally, feature map 412 is copied and concatenated with output from a feature map 442 to produce a feature map 444, as indicated by the dash-tailed rightward pointing arrow immediately to the right of feature map 412.

As indicated by the solid black rightward pointing arrow immediately to the right of feature map 414, a 3×3×3 convolution with stride 1 is performed on feature map 414 to produce a feature map 416. As indicated by the solid black rightward pointing arrow immediately to the right of feature map 416, a 3×3×3 convolution with stride 1 is performed on feature map 416 to produce a feature map 418.

As indicated by the downward pointing arrow beneath feature map 418, a 2×2×2 max pooling operation is performed on feature map 418 to produce a feature map 420, wherein feature map 420 is of half the spatial resolution of feature map 418. Additionally, feature map 418 is copied and concatenated with output from a feature map 436 to produce a feature map 438, as indicated by the dash-tailed rightward pointing arrow immediately to the right of feature map 418.

As indicated by the solid black rightward pointing arrow immediately to the right of feature map 420, a 3×3×3 convolution with stride 1 is performed on feature map 420 to produce a feature map 422. As indicated by the solid black rightward pointing arrow immediately to the right of feature map 422, a 3×3×3 convolution with stride 1 is performed on feature map 422 to produce a feature map 424.

As indicated by the downward pointing arrow beneath feature map 424, a 2×2×2 max pooling operation is performed on feature map 424 to produce a feature map 426, wherein feature map 426 is of one fourth the spatial resolution of feature map 424. Additionally, feature map 424 is copied and concatenated with output from a feature map 430 to produce a feature map 432, as indicated by the dash-tailed rightward pointing arrow immediately to the right of feature map 424.

As indicated by the solid black rightward pointing arrow immediately to the right of feature map 426, a 3×3×3 convolution is performed on feature map 426 to produce a feature map 428. As indicated by the solid black rightward pointing arrow immediately to the right of feature map 428, a 3×3×3 convolution with stride 1 is performed on feature map 428 to produce feature map 430.

As indicated by the upward pointing arrow immediately above feature map 430, a 2×2×2 up-convolution is performed on feature map 430 to produce a first half of feature map 432, while copied features from feature map 424 are used to produce a second half of feature map 432. Briefly, a 2×2×2 up-convolution (herein also referred to as a deconvolution, or up-sampling) with stride of 2 includes mapping a single feature in a single feature channel of an immediately preceding feature map to four features distributed amongst four feature channels in a current feature map (that is, output from a single feature channel is taken as input by four feature channels). Up-convolution/deconvolution/up-sampling comprises projecting a feature value from a single feature channel through a deconvolution filter (also herein referred to as a deconvolution kernel) to produce a plurality of outputs.

As indicated by the solid black rightward pointing arrow immediately to the right of feature map 432, a 3×3×3 convolution is performed on feature map 432 to produce a feature map 434.

As indicated in FIG. 4, a 3×3×3 convolution is performed on feature map 434 to produce feature map 436, and a 2×2×2 up convolution is performed on feature map 436 to produce a first half of feature map 438, while copied features from feature map 418 produce a second half of feature map 438. Further, a 3×3×3 convolution is performed on feature map 438 to produce a feature map 440, a 3×3×3 convolution is performed on feature map 440 to produce feature map 442, and a 2×2×2 up convolution is performed on feature map 442 to produce a first half of feature map 444, while copied and cropped features from feature map 412 are used to produce a second half of feature map 444. A 3×3×3 convolution is performed on feature map 444 to produce a feature map 446, a 3×3×3 convolution is performed on feature map 446 to produce feature map 448, and a 2×2×2 up convolution is performed on feature map 448 to produce a first half of feature map 450, while copied features from feature map 406 are used to produce a second half of feature map 450. A 3×3×3 convolution is performed on feature map 450 to produce a feature map 452, a 3×3×3 convolution is performed on feature map 452 to produce a feature map 454, and a 1×1×1 convolution is performed on feature map 454 to produce the output layer 456. Briefly, a 1×1×1 convolution includes a 1-to-1 mapping of feature channels in a first feature space to feature channels in a second feature space, wherein no reduction in spatial resolution occurs.

The output layer 456 may comprise an output layer of neurons, wherein each neuron may correspond to a voxel of a segmented medical image, and wherein an output of each neuron may correspond to a predicted anatomical feature or characteristic (or lack of the anatomical feature or characteristic) in a given location within the input medical image. For example, the output of a neuron may indicate whether the corresponding voxel of the segmented medical image is part of the liver or another anatomical feature.

In some embodiments, the output layer 456 may be fed back to an input layer of CNN 400. For example, the output layer from a previous iteration of CNN 400 is applied as input to a current iteration of CNN 400 as a feedback layer. The feedback layer may be included as another layer of the input image (at the same resolution) and thus may be included as part of the input image tile 402. For example, the input medical image 401 and the output layer of a previous iteration of CNN 400 (e.g., a buffered output, where buffered indicates that the output is stored in a buffer until it is used as an input to CNN 400) may be formed as a vector that is entered as input to CNN 400. In some examples, the input medical image that was used as input in the previous iteration of CNN 400 may also be included in the input layer.

In this way, CNN 400 may enable mapping of a medical image to an output in order to segment an anatomical feature of interest (e.g., the liver). The architecture of CNN 400 illustrated in FIG. 4 includes the feature map transformations which occur as an input image tile is propagated through the neuron layers of the convolutional neural network, to produce predicted output. The weights (and biases) of the convolutional layers in CNN 400 are learned during training, as will be discussed in more detail with reference to FIG. 5 below. Briefly, a loss function is defined to reflect the difference between the predicted output and the ground truth output. The difference/loss may be back projected to the CNN to update the weights (and biases) of the convolutional layers. A plurality of training data sets, comprising medical images and corresponding ground truth outputs, may be used to train CNN 400.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing a training duration. Regularization layers are used during CNN training and deactivated or removed during post-training implementation of the CNN 400. These layers may be interspersed between the layers/feature maps shown in FIG. 4 or may replace one or more of the shown layers/feature maps.

It should be understood that the architecture and configuration of CNN 400 shown in FIG. 4 is illustrative and non-limiting. Any appropriate neural network can be used, such as ResNet, recurrent neural networks, General Regression Neural Network (GRNN), etc. One or more specific embodiments of the present disclosure are described above in order to provide a thorough understanding. The skilled artisan will understand that specific details described in the embodiments can be modified when being placed into practice without deviating the spirit and scope of the present disclosure.

Figure 5:
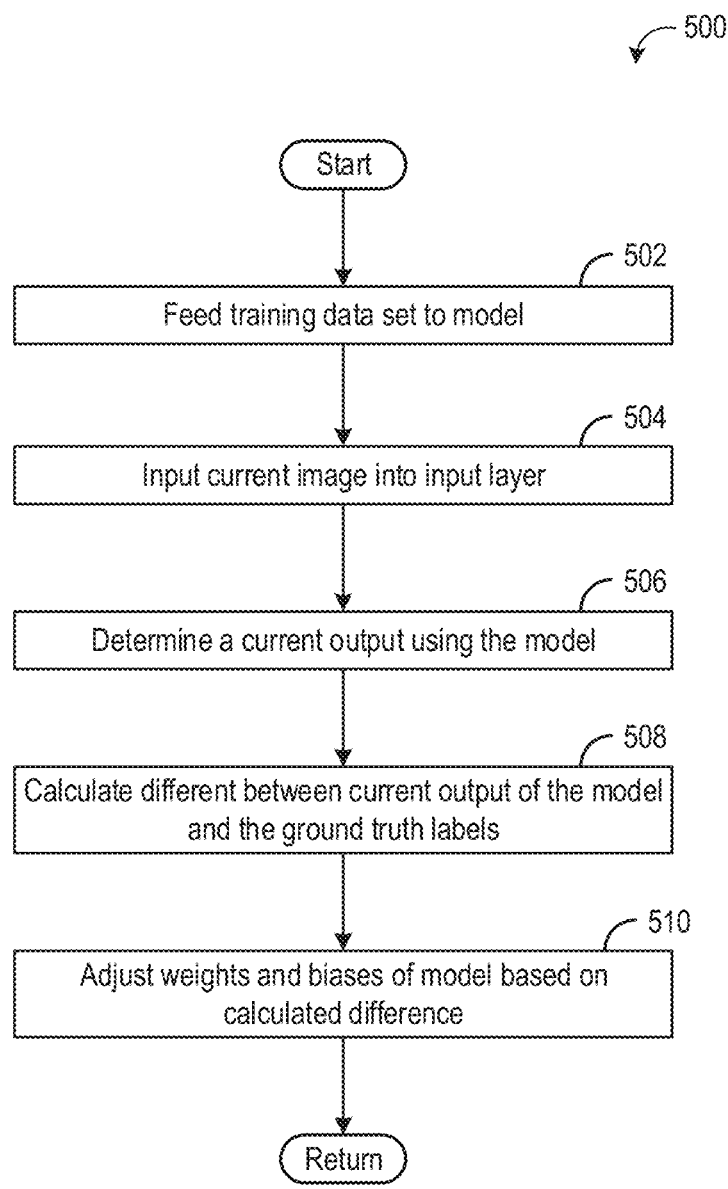
FIG. 5 is a flow chart illustrating a method for training a segmentation model, according to an embodiment.

Referring to FIG. 5, a flow chart of a method 500 for training a segmentation model (such as CNN 400 shown in FIG. 4) is shown, according to an exemplary embodiment. Method 500 may be implemented by training module 110 of FIG. 1, for example.

At 502, a training data set is fed to the segmentation model. The training data set may be selected from a plurality of training data sets and may include a current medical image, a prior model output, and corresponding ground truth labels. The prior model output may be determined based on a prior medical image that is acquired immediately prior to the current medical image, or from a prior image that is acquired before the current medical image but with one or more intermediate medical images acquired between the current medical image and the prior medical image. For example, the prior medical image may be a first frame of medical data collected by an imaging system, and the current medical image may be a fifth frame of medical data collected by the imaging system, with the second, third, and fourth frames of medical data collected by the imaging system discarded for the purposes of the training data set. As one example, the training data may include at least several hundred datasets in order to encompass high variabilities in terms of image acquisition parameters (e.g., injection phase variabilities, artifacts, peak x-ray source kilovoltage), anatomical structures, and pathologies.

A ground truth may include an expected, ideal, or "correct" result from a machine learning model based on input of the current medical image. In one example, in a machine learning model trained to identify anatomical structures (e.g., the liver) and/or features of the anatomical structures in medical images (e.g., a cancerous lesion within the liver), a ground truth output corresponding to a specific medical image may include an expert curated segmentation map of the medical image, which may include anatomical structures segmented from background as well as labels identifying each different tissue type of the anatomical structure. In another example, the ground truth output may be produced by an analytical method/algorithm. In this way, the ground truth labels may identify, for each image, the identity and location of each anatomical structure and/or feature in each image. In some embodiments, the training data set (and the plurality of training data sets) may be stored in the image processing system, such as in the medical image data 114 of image processing system 31 shown in FIG. 1. In other embodiments, the training data set may be acquired via a communicative coupling between the image processing system and an external storage device, such as via Internet connection to a remote server. As one example, the training data may include at least 600 datasets in order to encompass high variabilities in terms of image acquisition parameters (e.g., injection phase variabilities, artifacts, peak x-ray source kilovoltage), anatomical structures, and pathologies.

At 504, the current image of the training data set is input into an input layer of the model. In some embodiments, the current image is input into an input layer of a CNN having an encoder-decoder type architecture, such as CNN 400 shown in FIG. 4. In some embodiments, each voxel or pixel value of the current image is input into a distinct node/neuron of the input layer of the model.

At 506, a current model output, indicative of the identity and location of one or more anatomical structures and/or features in the current image, is determined using the current image and the model. For example, the model may map the input current image to the identity and location of the anatomical features by propagating the input current image from the input layer, through one or more hidden layers, and to an output layer of the model. In some embodiments, the output of the model comprises a matrix of values, with each value corresponding to an identified anatomical feature (or lack of identified feature) at a respective pixel or voxel of the input current image.

At 508, the difference between the current output of the model and the ground truth labels corresponding to the current image is calculated by the image processing system. In some embodiments, a difference between each output value, corresponding to a predicted anatomical feature of the input current image and an anatomical feature indicated by the ground truth labels is determined. The difference may be calculated according to a loss function, for example:

$$IoU = |S \cap T|/|S \cup T| \text{ or } DICE = 2 * \frac{|S \cap T|}{|S| + |T|}$$

wherein S is the ground truth labels and T is the predicted anatomical features. That is, the output of the model may include, for each pixel or voxel of the input current image, an indication of which anatomical feature (or lack thereof)

that pixel is part of. The ground truth labels may likewise include an indication of which identified anatomical feature that pixel is part of for each pixel of the current image. The difference between each output value and the ground truth labels may then be determined.

At 510, the weights and biases of the model are adjusted based on the difference calculated at 508. The difference (or loss), as determined by the loss function, may be back propagated through the model (e.g., the neural learning network) to update the weights (and biases) of the convolutional layers. In some embodiments, the back propagation of the loss may occur according to a gradient descent algorithm, wherein a gradient of the loss function (a first derivative, or approximation of the first derivative) is determined for each weight and bias of the model. Each weight (and bias) of the model is then updated by adding the negative of the product of the gradient determined (or approximated) for the weight (or bias) with a predetermined step size. Method 500 may then return. For example, method 500 may be repeated until the weights and biases of the model converge or until a rate of change of the weights and/or biases of the model for each iteration of method 500 are under a threshold.

In this way, method 500 enables a model to be trained to predict the location and/or other attributes (e.g., tissue characteristics) of one or more anatomical features from a current medical image, thereby facilitating automatic determination of identified anatomical feature characteristics in subsequent medical scans. In particular, method 500 may be used to train CNN 400 of FIG. 4 to segment the liver within an input medical image.

Referring now to FIG. 6, a flow chart of an example method 600 for analyzing and characterizing HCC lesions in a multi-phasic exam using image processing and deep learning models is shown. Method 600 may be implemented by one or more of the above disclosed systems, such as medical image processing system 100 of FIG. 1, CT system 200 of FIG. 2, and/or imaging system 300 of FIG. 3. In particular, method 600 provides a workflow for expediting and increasing an accuracy of HCC tumor detection and characterization in both pre-treatment and post-treatment patients.

At 602, method 600 includes obtaining liver images. As one example, the liver images may be obtained during a contrast-enhanced computed tomography (CT) scan (or CT exam). The contrast-enhanced CT scan may be used as a non-invasive method to assess liver tissue in a patient at risk of HCC, for example. As such, obtaining the liver images may include acquiring a series of CT images of the liver during different phases of the CT scan. For example, the CT images may be acquired before and during various phases after a contrast agent is injected in the patient. In particular, a first image may be acquired before the contrast agent is injected (e.g., at zero seconds post-injection) and may be referred to as an unenhanced (or non-contrasted) image. A second image may be acquired a short duration after the contrast agent is injected (e.g., at 20 seconds post-injection) and may be referred to as an arterial phase image. A third image may be acquired another short duration after the second image (e.g., at 50 seconds post-injection) and may be referred to as a portal phase image. A fourth image may be acquired a duration after the third image (e.g., at 150 seconds post-injection) and may be referred to as a delayed phase image. However, in other examples, the delayed phase image may not be obtained.

As elaborated above with respect to FIGS. 2 and 3, each image may be acquired by activating an x-ray source (e.g., x-ray source 204 of FIG. 2) configured to project a beam of x-ray radiation through the patient, particularly through the liver of the patient, to a detector array (e.g., detector array 208 of FIG. 2). The detector array measures x-ray attenuation by the patient, which may be used (e.g., by an image processor, such as image processor unit 210 of FIG. 2) to reconstruct the image. In some examples, additional processing, such as various corrections and normalizations, may be performed on the liver images prior to the processing described below.

At 604, method 600 includes performing liver and lesion registration. Because the contrast-enhanced CT scan is multi-phasic, the acquired images from the different phases may be aligned at 604 to account for patient movement during the scan. For example, even small movements, such as due to patient breathing, may result in shifting of the liver and the lesion within the scan view. As will be further described below with respect to FIG. 7, the registration may include first a rigid affine transform (three rotations and three translations) followed by a non-rigid transform (dense displacement field). As such, rigid and non-rigid registrations may be performed in order to more directly compare the lesion across images in order to more accurately track contrast agent dynamics within the lesion, as elaborated below.

At 606, method 600 includes performing liver segmentation on one of the liver images. For example, a fully convolutional neural network that is based on a 3D Unet architecture with ResNet connections and deep supervision may be used to segment the liver from other anatomical features in one of the series of obtained liver images. Further, a stochastic gradient descent with an adaptive learning rate method may be used as an optimizer along with a dice loss. Further still, affine transforms, elastic deformations, noise addition, and grayscale deformations may be performed on the obtained liver image. As one example, the liver segmentation may be performed using CNN 400 shown in FIG. 4. In some examples, a liver mask may be created to separate the segmented liver from the remaining pixels/voxels of the image. Because all of the liver images are aligned (e.g., at 604), the created liver mask may be applied to all of the other liver images in the series. As such, the liver segmentation performed on one of the liver images is valid for all of the liver images in the series. By performing the liver segmentation on one of the liver images after the liver images are registered, processing time and resources may be reduced. However, in alternative embodiments, the liver segmentation may be performed on each image of the plurality of images.

At 608, method 600 includes performing lesion segmentation on one of the liver images. As one example, the lesion segmentation may be a semi-automatic process where a user/physician provides a maximal axial diameter for the tumor within the segmented liver, such as via a user input device (e.g., user input device 32 of FIG. 1). Then, textural features within the given maximal axial diameter are extracted (for example, using mean, median, standard deviation, and edge detection filters) and clustered using a k-means approach, which may output a texture map. This texture map may be used to define "object" and "background" labels (or seeds) that are further used as inputs for a random walker algorithm. The random walker algorithm may define an edge between the lesion and healthy liver tissue (e.g., the parenchyma) based on the similarity or difference between neighboring pixels. Thus, the lesion may be segmented from the surrounding parenchyma in each of the series of obtained liver images. In some examples, a lesion mask may be created to separate the segmented lesion from the remaining pixels/voxels of the image. Because all of the liver images are aligned (e.g., at 604), the created lesion mask may be applied to all of the other liver images in the series. As such, the lesion segmentation performed on one of the liver images is valid for all of the liver images in the series. By performing the lesion segmentation on one of the liver images after the liver images are registered, processing time and resources may be reduced. However, in alternative embodiments, the lesion segmentation may be performed on each image of the plurality of images.

At 610, method 600 includes creating and characterizing a reference region of interest (ROI) on each liver image. Once the different phases of the contrast-enhanced CT exam are registered and resampled to the same resolution, the dynamics of the contrast agent inside the tumor can be tracked. To characterize the dynamics of the contrast agent inside the tumor, a reference measurement extracted from the liver parenchyma at the surrounding of the tumor is used. Thus, the reference ROI is created and characterized for each liver image in the series. Creating the reference ROI includes applying a distance transform from the lesion mask to create a ROI at a distance between 10 mm and 30 mm of the tumor. This ROI is constrained to lie inside the liver mask. By creating the ROI the distance away from the tumor, a likelihood that portions of the lesion are inadvertently included in the reference ROI is decreased. As such, the reference ROI is expected to reflect contrast agent uptake dynamics of the liver parenchyma.

Characterizing the reference ROI includes extracting statistics from the parenchyma, including mean, standard deviation, noise autocorrelation, and number of pixels (or voxels). However, some structures can introduce some bias (other tumors, vessels, etc.) and hence, robust measurements are used. The mean value may be estimated from the mode of a ROI histogram regularized by a Gaussian filter. For the standard deviation, a half full width half maximum may be used as a robust estimator. As another example, noise autocorrelation also may be calculated and used in lesion analysis, as will be elaborated below.

By automatically placing the reference ROI, there is no reliance on the user for correct placement, its position around the tumor is precisely controlled, and its size is much larger than a spherical ROI that can be defined manually. As a result, an accuracy and repeatability of the reference ROI measurements is increased, which also increases an accuracy and repeatability of tumor measurements made therefrom. An illustrative example of creating and characterizing a reference ROI will be described with respect to FIG. 8.

At 612, method 600 includes performing lesion sub-segmentation. An HCC lesion can have heterogeneous tissues, including viable (both arterial and portal), necrotic, chemoembolized (if treated with a chemoembolization product), or undefined tissues. The dynamics of the contrast agent in each tissue is different through time. For example, necrotic tissues have mean grayscale values that remain below the reference ROI throughout the multi-phase exam, whereas typical viable tissues are similar, higher, and lower during the unenhanced, arterial, and portal phases, respectively. Hence, pixels/voxels will be assigned to a different tissue class depending on ad hoc rules defined by physicians (e.g., hepatologists) regarding the expected contrast agent dynamics in each tissue class (or type). As will be described below with respect to FIG. 9, the images may undergo noise reduction and filtering in order to reduce noise while preserving contrast information. The contrast information may enable a temporal profile to be generated for each pixel (or voxel) to classify the tissue contained therein. For example, the mean grayscale value of each pixel/voxel may be tracked across each exam phase to determine how the grayscale value (e.g., pixel/voxel intensity) changes relative to the reference ROI during each phase. Then, the temporal profile of a given pixel/voxel may be compared to the criteria defined for each tissue class in order to determine the type of tissue in that pixel/voxel. Further, in some examples, performing the sub-segmentation may include calculating a proportion of each tissue type within the lesion in order to give an overall indication of the tissue composition. An example HCC lesion that has undergone segmenting and sub-segmenting is show in FIG. 10 and will be described below.

At 614, it is determined if the lesion is in a pre-treatment state. The pre-treatment state corresponds to a naïve lesion that has not undergone chemotherapy, such as trans-arterial chemoembolization (TACE) or drug-eluting bead trans-arterial chemoembolization (DEB-TACE), or any other interventional procedures, such as radioembolization or radiofrequency ablation. As one example, TACE includes injecting an embolic agent such as Lipiodol (e.g., ethiodized oil) into an artery directly supplying the tumor (e.g., the hepatic artery) to block the blood supply to the tumor, thereby inducing cell death (e.g., necrosis). Thus, a tumor that has undergone TACE, DEB-TACE, radioembolization, and/or radiofrequency ablation is in a post-treatment state, whereas a tumor that has not undergone TACE, DEB-TACE, radioembolization, or radiofrequency ablation may be in the pre-treatment state. In some examples, the user may manually indicate whether the lesion is in the pre-treatment state. As an example, when entering in patient information for the CT scan, the user may be prompted to select one of "pre-treatment lesion" and "post-treatment lesion." As another example, the system may automatically determine whether the lesion is in the pre-treatment state based on the type of assessment ordered (e.g., LI-RADS feature extraction for a pre-treatment tumor or a LI-RADS treatment response feature extraction for a post-treatment tumor). As still another example, the system may infer whether the lesion is in the pre-treatment state or the post-treatment state based on data from an electronic health record (EHR) associated with the patient. For example, the EHR may include previously performed exams, diagnoses, and current treatments, which may be used to determine whether or not the lesion is the pre-treatment state.

If the lesion is in the pre-treatment state, method 600 proceeds to 616 and includes extracting LI-RADS features. The LI-RADS features include a 2D lesion diameter, which may be measured from the lesion segmentation and represents a size of the lesion, arterial phase hyperenhancement (APHE), which occurs during the arterial phase, wash-out (WO), which occurs during the portal and/or delayed phases, and the presence of an enhancing capsule (CAP), which occurs during the portal and/or delayed phases. APHE, WO, and CAP are detected based on a contrast between the lesion and its surroundings (e.g., the reference ROI created and characterized at 610), which is used to assess whether the two distributions are similar or different. The probability that the two distributions are different takes into consideration the change in Hounsfield units, the noise standard deviation and autocorrelation, and the lesion/reference ROI size. These parameters are estimated for both the reference ROI and on the tumor viable tissues, as determined through the sub-segmenting at 612.

The probabilities of APHE, WO, and CAP are computed through confidence intervals of the means. Under a normal distribution hypothesis, the upper limit (e.g., bound) of a distribution $N(\mu,\sigma)$ is defined by Equation 1:

$$\mu_{sup}(\alpha) = \mu + \frac{\sigma}{\sqrt{N_{eq}}} \times t(N_{eq} - 1, \alpha) \qquad \text{(Equation 1)}$$

where $\mu$ is the mean value of a given distribution, $\sigma$ is the standard deviation of the given distribution, $\alpha$ is the confidence, t is the Student's one tail t-distribution, and $N_{eq}$ is the number of independent voxels in the data ($N_{eq}$ considers the ROI size, the noise auto-correlation and the mode statistical efficiency, which is around 20%). Equation 1 means that there is a probability of 60% that the true distribution mean is contained into the interval]–∞,$\mu_{sup}$].

Similarly, the lower limit of a distribution is defined by Equation 2:

$$\mu_{inf}(\alpha) = \mu - \frac{\sigma}{\sqrt{N_{eq}}} \times t(N_{eq} - 1, \alpha) \qquad \text{(Equation 2)}$$

where $\mu$ is the mean value of a given distribution, $\sigma$ is the standard deviation of the given distribution, $\alpha$ is the confidence, t is the Student's one tail t-distribution, and $N_{eq}$ is the number of independent voxels in the data.

Next, the confidence at 60% is computed such that $\mu_1$ $sup(\alpha)=\mu_{2\ inf}(\alpha)$. In this example, $\mu_{1\ sup}$ is the upper bound of a first distribution (e.g., the reference ROI) and $\mu_{2\ inf}$ is the lower bound of a second distribution (e.g., the viable portion of the lesion). Therefore, $\alpha^2$ corresponds to the probability of having an APHE a wash-out, or an enhancing capsule. When the probability is at least a threshold percentage, it is determined that the corresponding feature (e.g., APHE, WO, or CAP) is present, whereas when the probability is less than the threshold percentage, it is determined that the corresponding feature is absent. The threshold percentage refers to a probability above which it can be assumed with high confidence that the corresponding feature is present. As one non-limiting example, the threshold percentage is 90%. An example of the LI-RADS feature extraction is shown in FIG. 11 and will be described below.

At 618, method 600 includes determining a LI-RADS score based on the LI-RADS features extracted at 616. The determined LI-RADS score may be a preliminary score or score range that helps guide the physician in determining a final LI-RADS score, at least in some examples. As such, the physician may change the score if desired. The LI-RADS score may be determined using known criteria that relate the LI-RADS features, including the lesion size and the presence or absence of each of APHE, WO, and CAP, to a relative risk of HCC. The scoring ranges from LR-1 (benign, not HCC) to LR-5 (definitely HCC). As an illustrative example, a lesion having a size of 15 mm with APHE, WO, and no enhancing capsule corresponds to a LI-RADS score of LR-4 (probably HCC). By determining the LI-RADS score based on the automatically extracted LI-RADS features, a mental burden is decreased for the physician, and a reproducibility and accuracy of the scoring is increased.

At 620, method 600 includes outputting images of the sub-segmented HCC lesion and a LI-RADS report. For example, the sub-segmented HCC lesion, including tissue type annotations, may be output to a display device (e.g., display device 33 of FIG. 1) for display to the user/ physician. The LI-RADS report may include one or more of the determined APHE probability, the determined wash-out probability, a size and tissue composition of the lesion, and LI-RADS score, which also may be output to the display device. As another example, outputting images of the sub-segmented HCC lesion and the LI-RADS report may include saving the images and the LI-RADS report to a specified storage location. As mentioned above, the LI-RADS report may be used by the physician to diagnose the patient, including a degree of malignancy of the lesion. Method 600 may then end.

Returning to 614, if the lesion is not in the pre-treatment state, then the lesion is in the post-treatment state (e.g., after TACE or another treatment), and method 600 proceeds to 622 and includes comparing the current HCC lesion sub-segmentation with the HCC lesion sub-segmentation from a previous acquisition. For example, a proportion of the remaining viable tissue, a proportion of necrotic tissue, and a proportion of chemoembolized tissue may be compared to values determined for the same HCC lesion prior to TACE (or the current round of treatment). However, in other examples, the current HCC lesion sub-segmentation may not be compared to the previous HCC lesion sub-segmentation, such as when no previous data is available. Further, in some examples, LI-RADS features may also be extracted post-treatment in order to compare pre- and post-treatment lesion size and APHE, WO, and CAP probabilities.

At 624, method 600 includes determining a treatment response based on the comparison preformed at 622. As one example, the treatment response may include a response score determined based on pre-defined criteria, such as a percent change in the proportion of viable tissue in the tumor and/or a percent change in the proportion of necrotic tissue in the tumor following treatment (e.g., TACE). When no previous data is available for the given lesion, the treatment response may be inferred based on data for other HCC lesions having similar post-treatment tissue compositions. The response score may give an indication of patient prognosis. As one example, the response score may be used to determine whether additional treatments with the same chemoembolic agent are expected to further reduce the proportion of viable tissue in the tumor, reduce the tumor size, and/or clear the tumor. For example, higher response scores may indicate that the tumor is highly responsive to the current course of treatment. As another example, the response score may suggest considering other treatment options, such as when the response score is lower (e.g., the tumor is relatively non-responsive to the current course of treatment). Thus, the determined treatment response may help guide a physician in determining a treatment course for the patient.

At 626, method 600 includes outputting image of the sub-segmented HCC lesion and a treatment report. For example, the sub-segmented HCC lesion and the treatment report may be output to the display device and/or a storage location, as described above at 620. The treatment report may include one or more of the determined treatment response, the response score, and treatment recommendations. Method 600 may then end.

In this way, the method uses image processing and deep learning methods to speed up and increase an efficiency of tumor detection and characterization. Overall, HCC tumors may be more accurately characterized, and variation may be decreased. As a result, positive patient outcomes may be increased.

Next, FIG. 7 shows an example workflow of a deep learning network 700 for aligning images obtained during a multi-phasic imaging exam using both rigid and non-rigid registration. The deep learning network 700 includes a first network portion 702 and a second network portion 704. In the example shown, the first network portion 702 performs the rigid registration via an affine transformation, and the second network portion 704 performs the non-rigid registration via a voxel morph diffeomorphic architecture.

A legend 799 shows various elements included in the deep learning network 700. As indicated by the legend 799, the deep learning network 700 includes a plurality of convolutional layers/feature maps connected by one or more operations. The operations receive input from either an external file (e.g., an input image) or a previous layer/feature map and transform/map the received input to produce a next layer/feature map. Each layer/feature map may comprise a plurality of neurons. In some embodiments, each neuron may receive input from a subset of neurons of a previous layer/feature map and may compute a single output based on the received inputs. The output may be propagated/mapped to a subset or all of the neurons in a next layer/feature map. A layer/feature map may be described using spatial dimensions, such as length, width, and depth, wherein the dimensions refer to the number of neurons comprising the feature map (e.g., how many neurons long, how many neurons wide, and how many neurons deep, a specified layer/feature map is).

As shown in the legend 799, diagonally shaded feature maps (e.g., feature maps 710, 712, 714, 730, 732, 734, and 736) include 3D convolution (CONV 3D) with batch normalization (BN) and leaky ReLu activation (LEAKY RELU). Lighter dot shaded feature maps (e.g., feature maps 736, 738, 740, and 742) include 3D transpose convolution (CONV 3D TRANSPOSE) with concatenation (CONCAT) and 3D convolution with leaky ReLu activation (CONN 3D+LEAKY RELU). Diamond shaded feature maps (e.g., feature maps 716a, 716b, 718a, and 718b) include 3D convolution. Darker dot shaded feature maps (e.g., feature maps 720a and 720b) include global average pooling. A vertically shaded feature map (e.g., a feature map 744) includes a velocity field. An unshaded feature map (e.g., a feature map 746) includes an integration layer.

A source image (e.g., a moving imaging) 706a and a target image (e.g., a fixed image) 708a are inputs for the first network portion 702. A source cropped image 706b and a target cropped image 708b are outputs of the first network portion 702 and inputs for the second network portion 704. The source image 706a and the target image 708a may be selected from a series of liver images obtained during a multi-phasic CT scan, as described above with respect to FIG. 6. For example, the target image 708a may serve as a template (e.g., reference configuration) to which the source image 706a is aligned. Thus, the first network portion 702 finds the best rigid transformation to apply on the moving image (the source image) to match the fixed image (the target image). A same image may be used as the target image 708a for aligning all of the remaining images in the series of liver images. One of the remaining images (e.g., that is not the target image 708a) may be selected to be the source image 706a until all of the remaining images have undergone the registration.

The source image 706a and the target image 708a are input into the feature map 710. The resulting global average pooling feature map 720a undergoes six parameter transforms 722, including three rotational transformations and three translations (e.g., in x, y, and z). The resulting global average pooling feature map 720b undergoes six parameter evaluations 724 that result in values for bounding box centers ("BB_centers") and result in values for bounding box sizes ("BB_sizes"). The resulting rotated and translated layer is input into a spatial transform 726 along with the source image 706a. The output of the spatial transform 726, the bounding box centers, the bounding box sizes, and the target image 708a are input into a cropping function 728 in order to crop the source image and the target image with the same bounding box. The cropping function 728 outputs the source cropped image 706b and the target cropped image 708b.

The source cropped image 706b and the target cropped image 708b are input into feature map 730 of the second network portion 704. The second network portion 704 finds the best non-rigid deformation field to apply on the moving image to match the fixed image. The velocity field layer feature map 744 and the integration layer feature map 746 are used to generate a deformation field 748, which provides a matrix of displacement vectors for each voxel (or pixel for 2D images) in the source cropped image 706b relative to each analogous voxel in the target image cropped 708b. The deformation field 748 and the source cropped image 706b are input into a spatial transform 750, which outputs a deformed image 752. The deformed image 752 comprises the source cropped image 706b aligned to the target cropped image 708b. Thus, the deformed image 752 is the output of the second network portion 704 and the overall output of the deep learning network 700 and has undergone both rigid registration (e.g., via the first network portion 702) and non-rigid registration (e.g., via the second network portion 704).

FIG. 8 schematically shows an example workflow 800 for creating a characterizing a reference ROI in a medical image. Specifically, the reference ROI is created within a medical image 802 obtained during a CT scan of a patient's liver. The medical image 802 undergoes processing and analysis to segment the liver and a lesion within the liver, as described above with respect to FIG. 6, resulting in a liver mask 804 and a lesion mask 806. The liver mask 804 shows the liver in white and non-liver portions of the medical image 802 in black. The liver mask 804 separates pixels/voxels corresponding to the non-liver portions of the medical image 802 from those within the liver. In this way, the liver mask 804 hides the non-liver portion of the medical image 802 from the remainder of the workflow 800 so that these pixels/voxels are not considered for reference ROI creation and characterization. Similarly, the lesion mask 806 segregates the pixels/voxels corresponding to the lesion from other liver tissues and shows the lesion in white and the remainder of the medical image, including other portions of the liver, in black.

A distance transform 808 is applied to the lesion mask 806 to place a distance between the edge of the lesion and the reference ROI. The distance may be in a range between 10 mm and 30 mm, for example. This creates a preliminary reference ROI 810, which is shown as a 3D volume. The preliminary reference ROI 810 excludes voxels within the distance transform 808, including all of the voxels within the lesion mask 806. The liver mask 804 and the preliminary reference ROI 810 are input into an intersection function 812, which refines the preliminary reference ROI 810 by constraining it to lie within the liver mask 804. The intersection function 812 outputs a reference ROI 814, shown as a 3D volume. Because the reference ROI 814 excludes voxels within the lesion mask 806 (and the distance from the lesion mask 806) and is constrained to the liver mask 804, the reference ROI 814 includes voxels corresponding to healthy liver tissue.

Statistics 816 are performed on the created reference ROI 814. The statistics may include (but are not limited to) estimating a mean intensity value, a standard deviation of the intensity values, a noise autocorrelation, and a number of pixels/voxels in the ROI. The mean value may be estimated from the mode of an ROI histogram, which may be normalized by a Gaussian filter. The relatively large size of the reference ROI (e.g., compared with a volume that can be manually selected by a user/physician) provides a robust estimation of the mean and standard deviation, as its size makes it less susceptible to the effects of structures other than liver parenchyma (e.g., other tumors, vessels) and registration errors. The workflow 800 may output a reference ROI analysis 818, which may include the statistics 816. The reference ROI analysis 818 may be used for subsequent HCC lesion sub-segmentation and characterization, as described above with respect to FIG. 6 and elaborated below.

FIG. 9 schematically shows an example workflow 900 for performing HCC lesion sub-segmentation and characterization in images obtained during a contrast-enhanced multi-phasic CT scan of a liver. For example, workflow 900 may be performed by an image processing system (e.g., image processing system 100 of FIG. 1) as a part of method 600 of FIG. 6.

At 902, a plurality of images are input into the workflow 900. Each image comprises one image acquired during one phase of the multi-phasic exam, as elaborated above with respect to FIG. 6. Three images are shown in the example of FIG. 9: an unenhanced (UE) image 904a, an arterial phase image (Art) 906a, and a portal phase image (Port) 908a. Each image is averaged at 910, and a guided filter 911 is used to perform noise reduction and filtering on each averaged image at 912. The guided filter 911 may include a joint bilateral filter with an average image used as a guided image, enabling the reduction of the noise while preserving contrasts. The resulting filtered images are shown at 914. Specifically, 914 shows a filtered unenhanced image 904b, a filtered arterial phase image 906b, and a filtered portal phase image at 908b.

A pixel-wise (or voxel-wise) temporal analysis is performed at 916. That is, an intensity of each pixel (or voxel) may be tracked through the series of filtered images to generate a temporal profile, which is shown as a graph 918. Graph 918 includes time as the horizontal axis, with the time points at which the different images are acquired labeled on the horizontal axis. The vertical axis represents a change in the intensity of the given pixel (e.g., delta Hounsfield units, or HU) relative to the reference ROI created and analyzed using the workflow of FIG. 8, for example. Each line on the graph shows a different pixel.

At 920, each pixel (or voxel) is classified as a particular type of tissue based on its temporal profile. Possible tissue types include necrotic, viable arterial, viable portal, chemo-embolized (e.g., following trans-arterial chemoembolization with a chemotherapeutic agent, such as Lipiodol), peripheral enhancement, undefined, and parenchyma. The dynamics of the contrast agent over time is different in each tissue type. As an example, necrotic tissues have mean grayscale values that remain less than that of the reference ROI across time, whereas typical viable tissues have mean grayscale values that are similar, higher, and lower than that of the reference ROI during the unenhanced, arterial, portal phases, respectively. Hence, pixels (or voxels) are assigned to different classes at 920 based on ad hoc classification rules created by qualified physicians (e.g., hepatologists or oncologists). In this way, the lesion may be sub-segmented based on the tissue type within the lesion. The resulting sub-segmented lesion may be output as an image and/or as a report containing quantitative and/or qualitative information regarding the lesion tissue composition.

FIG. 10 shows example images 1000 of an HCC lesion that has been segmented and sub-segmented, such as according to the method of FIG. 6 and using the workflow outlined in FIG. 9. In particular, the images 1000 show a post-treatment lesion. A first image 1002 shows the segmented lesion, including a lesion boundary 1006. The lesion boundary 1006 separates the lesion from liver tissue surrounding the lesion. A second image 1004 shows the sub-segmented lesion. The sub-segmented lesion includes different tissue classifications for different portions of the segmented lesion. A viable region 1008 is outlined by a dotted border, a chemoembolized region 1010 is outlined by a longer dashed border, and a necrotic region 1012 is outlined by a shorter dashed border. As described above with respect to FIG. 6, in some examples, an image processing system (e.g., image processing system 100 of FIG. 1) may use the sub-segmented lesion to determine a percentage of the tumor that remains viable and/or estimate an effectiveness of the treatment.

FIG. 11 shows a plurality of example liver images 1100 obtained during a multi-phasic CT scan and features extracted by an image processing system, such as image processing system 100 of FIG. 1, using image processing and deep learning methods to analyze the images, such as according to the method of FIG. 6. In particular, the plurality of example liver images 1100 are arranged in a grid, with each row corresponding to a series of four images obtained during the multi-phasic CT scan and the resulting feature analysis. Each column represents liver images from a single phase of the CT scan or a given feature analysis. For example, a first row 1102 shows a first series of liver images and the resulting feature analyses, a second row 1104 shows a second series of liver images and the resulting feature analyses, a third row 1106 shows a third series of liver images and the resulting feature analyses, and a fourth row 1108 shows a fourth series of liver images and the resulting feature analyses. For each of the series of liver images, a first column 1110 shows a non-contrasted (NC) image, a second column 1112 shows an arterial phase image, a third column 1114 shows a portal phase image, a fourth column 1116 shows a delayed phase image, a fifth column 1118 shows lesion sub-segmentation, a sixth column 1120 shows a viable region and an arterial phase hyper-enhancement (APHE) probability, a seventh column 1122 shows a viable region and a wash-out (WO) probability, and an eighth column 1124 shows a peripheral enhancement region and a capsule (CAP) probability. In some examples, the image processing system may display all or some of the example liver images 1100 to a user, such as via a display device (e.g., display device 33 of FIG. 1).

The APHE probabilities in column 1120 are determined from the arterial phase images (column 1112), the wash-out probabilities in column 1122 are determined from the portal phase images (column 1114), and the capsule probabilities in column 1124 are determined from the delayed phase images (column 1116), such as described at 616 of FIG. 6. These probabilities are influenced by the difference in HU (e.g., the pixel intensity) between the lesion and the surrounding tissue, the noise standard deviation, the noise autocorrelation, and the region size. For example, when the difference in HU is higher, the probability is higher. As another example, as the noise increases, the probability decreases. As a further example, higher noise autocorrelation results in smaller probabilities. As still another example, the probability decreases as the region size decreases. In the example of FIG. 11, probability of at least 90% triggers positive identification of the corresponding feature, whereas probabilities less than 90% denotes that the corresponding feature is absent.

Looking first at the first series of liver images in the first row 1102, the non-contrasted image (column 1110), the arterial phase image (column 1112), the portal phase image (column 1114), and the delayed phase image (column 1116) are registered with each other, such as described with respect to FIG. 7. A boundary 1126 of the lesion is shown in the arterial phase image (column 1112), which may be determined by extracting textural features and using a random walker segmentation algorithm, as described above with respect to FIG. 6. As shown, the segmented lesion has pixel intensities more similar to the healthy tissue surrounding the lesion in the arterial phase image (column 1112) than in the non-contrasted image (column 1110). Additionally, the portal phase image (column 1114) shows darkening of the lesion (e.g., a decrease in pixel intensity) relative to the healthy tissue surrounding the image, producing a strong contrast between the lesion and the surrounding tissue. The pixel intensity in the lesion remains relatively low in the delayed phase image (column 1116). In the portal and delayed phase images, the lesion periphery is brighter than the surrounding tissues.

The image processing system generates a temporal profile for each pixel in the segmented lesion, such as described above with respect to FIG. 9, and uses this temporal profile to sub-segment the lesion. The resulting sub-segmented lesion shown in column 1118 includes the lesion boundary 1126, an arterial viable region within dotted boundary 1128, a portal viable region within dashed boundary 1130, a peripheral enhancement region within long-dashed boundary 1132 and a necrotic region within short-dashed boundary 1134. The arterial viable region is also shown in column 1120, which shows a 75% APHE probability. Therefore, APHE is determined to be absent because the probability is less than 90%. The portal viable region is also shown in column 1122, which shows a 100% wash-out probability (e.g., WO is present). The peripheral enhancement region is also shown in column 1124, which shows a 100% capsule probability (e.g., the capsule is present). The image processing system may determine the APHE, the wash-out and capsule probabilities as described above with respect to FIG. 6. Because the lesion shown in the first row 1102 has a diameter <20 mm, no APHE, and has WO and an enhancing capsule, the image processing system may score the lesion as LR-4.

The second series of liver images in the second row 1104 is arranged as described above. A boundary 1134 of the lesion is shown in the arterial phase image (column 1112). As shown, the segmented lesion has pixel intensities more similar to the healthy tissue surrounding the lesion in the arterial phase image (column 1112) than in the non-contrasted image (column 1110). Further, in the arterial phase image (column 1112), the segmented lesion in the second series of liver images (second row 1104) has pixel intensities more similar to the healthy tissue surrounding the lesion than the segmented lesion in the first series of liver images (first row 1102). Similar to the first series of liver images (first row 1102), the portal phase image (column 1114) shows darkening of the lesion (e.g., a decrease in pixel intensity) relative to the healthy tissue surrounding the image, producing contrast between the lesion and the surrounding tissue and a brightening of the periphery of the lesion. The pixel intensity in the lesion remains relatively low in the delayed phase image (column 1116).

The resulting sub-segmented lesion shown in column 1118 includes the lesion boundary 1134, an arterial viable region within dotted boundary 1136, a portal viable region within dashed boundary 1138, a peripheral enhancement region within long-dashed boundary 1140, and necrotic regions within short-dashed boundary 1142. The arterial viable region is also shown in column 1120, which shows a 100% APHE probability. The portal viable region is also shown in column 1122, which shows 100% wash-out probability. The peripheral enhancement region is also shown in column 1124, which shows 100% capsule probability. Because the lesion shown in the second row 1104 has a diameter between 10 and 20 mm and has APHE, WO, and an enhancing capsule, the image processing system may score the lesion as LR-5.

Looking now at the third series of liver images in the third row 1106, a boundary 1144 of the lesion is shown in the arterial phase image (column 1112). As shown, the segmented lesion has higher (e.g., brighter) pixel intensities in the arterial phase image (column 1112) than in the non-contrasted image (column 1110). Further, the segmented lesion in the arterial phase image (column 1112) of the third series of liver images (third row 1106) has higher pixel intensities than the segmented lesion in the arterial phase image (column 1112) of the first series of liver images (first row 1102) and the segmented lesion in the second series of liver images (second row 1104). In the third series of liver images, there is not noticeable contrast between the lesion and the parenchyma in the portal phase image (column 1114) nor in the delayed phase image (column 1116). Furthermore, there is not noticeable bright contrast between the lesion periphery and the parenchyma in the portal phase image (column 1114) nor in the delayed phase image (column 1116).

The resulting sub-segmented lesion shown in column 1118 includes the lesion boundary 1144, an arterial viable region within dotted boundary 1146, which substantially overlaps with the lesion boundary 1144, and a portal viable region within dashed boundary 1148. The arterial viable region is also shown in column 1120, which shows a 100% APHE probability. The portal viable region is also shown in column 1122, which shows 60% wash-out probability. There is no visible peripheral enhancement region column 1124, giving a 0% capsule probability. Because the lesion shown in the third row 1106 has a diameter less than 10 mm and has APHE without WO and without an enhancing capsule, the image processing system may score the lesion as LR-4.

The fourth series of liver images in the fourth row 1108 shows a boundary 1150 of the lesion in the arterial phase image (column 1112). As shown, the lesion is substantially indistinguishable from the parenchyma in the non-contrasted image (column 1110) and has higher pixel intensities in the arterial phase image (column 1112) than in the non-contrasted image (column 1110). Further, the segmented lesion in the arterial phase image (column 1112) of the fourth series of liver images (fourth row 1108) has higher pixel intensities than the segmented lesion in the arterial phase image (column 1112) of the first series of liver images (first row 1102), the second series of liver images (second row 1104), and the third series of liver images (third row 1106). In the fourth series of liver images, the lesion has a perimeter of higher intensity pixels and a central region of lower intensity pixels (e.g., relative to the perimeter) in the portal phase image (column 1114) and in the delayed phase image (column 1116).

The resulting sub-segmented lesion shown in column 1118 includes the lesion boundary 1150, an arterial viable region within dotted boundary 1152, which substantially overlaps with the lesion boundary 1150, a portal viable region within dashed boundary 1154, and a peripheral enhancement region within long-dashed boundary 1156. The arterial viable region is also shown in column 1120, which shows a 100% APHE probability. The portal viable region is also shown in column 1122, which shows a 45% wash-out probability. The peripheral enhancement region is also shown in column 1122, which shows 100% capsule probability. Because the lesion shown in the fourth row 1108 has a diameter between 10 and 20 mm and has APHE without WO and with an enhancing capsule, the image processing system may score the lesion as LR-4 or LR-5.

A technical effect of automatically characterizing liver cancer lesions using deep learning approaches is that an accuracy of the characterization may be increased, thereby increasing an accuracy and timeliness of patient treatment decisions.

An example provides a method, comprising acquiring a plurality of medical images over time during an exam; registering the plurality of medical images; segmenting an anatomical structure in one of the plurality of medical images after registering the plurality of medical images; creating and characterizing a reference region of interest (ROI) in each of the plurality of medical images; determining characteristics of the anatomical structure by tracking pixel values of the segmented anatomical structure over time; and outputting the determined characteristics on a display device.

In an example, registering the plurality of medical images includes applying rigid and non-rigid registrations to a source image and a target image, the source image and the target image selected from the plurality of medical images.

In examples, the method further comprises after registering the plurality of medical images and segmenting the anatomical structure, segmenting a lesion within the anatomical structure. In one example, segmenting the anatomical structure includes using a convolutional neural network, and segmenting the lesion includes extracting and clustering textural features based on a received maximal axial diameter of the lesion, the textural features including at least one of a mean, a median, and a standard deviation of the pixel values within the segmented anatomical structure in each of the plurality of medical images. In some examples, the exam is a multi-phasic contrast-enhanced computed tomography (CT) exam, and segmenting the anatomical structure includes segmenting the liver. As an example, the multi-phasic contrast-enhanced CT exam includes an unenhanced phase, an arterial phase after the unenhanced phase, a portal phase after the arterial phase, and a delayed phase after the portal phase, and the plurality of medical images include a first CT image of the liver obtained during the unenhanced phase, a second CT image of the liver obtained during the arterial phase, a third CT image of the liver obtained during the portal phase, and a fourth CT image of the liver obtained during the delayed phase.

In examples, the reference ROI comprises tissue outside of the segmented lesion and within the segmented liver, wherein the characteristics of the anatomical structure include a tissue classification of each portion of the segmented lesion, and wherein determining the characteristics of the anatomical structure by tracking the pixel values of the segmented anatomical structure over time includes determining the tissue classification of each portion of the segmented lesion based on a value of each pixel within the portion relative to the reference ROI in each of the plurality of medical images. As an example, the tissue classification is one of necrotic, viable, chemoembolized, undefined, peripheral enhancement, and parenchymal.

In one example, the characteristics of the anatomical structure further include an effect of a treatment, and determining the characteristics of the anatomical structure by tracking the pixel values of the segmented anatomical structure over time further includes determining the effect of the treatment by comparing the tissue classification of each portion of the segmented lesion from a first exam and with the tissue classification of each portion of the segment lesion from a second exam, the first exam performed before the treatment and the second exam performed after the treatment.

In one example, the characteristics of the anatomical structure further include Liver Imaging Reporting and Data System (LI-RADS) scores, and determining the characteristics of the anatomical structure by tracking the pixel values of the segmented anatomical structure over time further includes: determining arterial phase hyperenhancement (APHE), wash-out, and capsule probabilities of a contrast agent used in the multi-phasic contrast-enhanced CT exam based on the pixel values of the segmented lesion relative to the reference ROI in each of the plurality of medical images.

An example method comprises receiving a series of liver images from a multi-phasic exam; aligning the series of liver images; segmenting the liver and a lesion within the series of aligned liver images; sub-segmenting the lesion based on changes in pixel values of the segmented lesion across the series of aligned liver images; and outputting an analysis of the sub-segmented lesion. In examples, the series of liver images include one liver image from each phase of the multi-phasic exam, and segmenting the liver includes: defining a boundary of the liver in one image of the series of aligned liver images using a convolutional neural network; and applying the boundary of the liver to each additional image in the series of aligned liver images. In one example, segmenting the lesion includes: defining a boundary of the lesion within the boundary of the liver in the one image of the series of aligned liver images based on textural features of the one image, the textural features including at least one of a mean, a median, and a standard deviation of the pixel values within the boundary of the liver in the one image; and applying the boundary of the lesion to each additional image in the series of aligned liver images.

In examples, sub-segmenting the lesion based on the changes in pixel values of the segmented lesion across the series of aligned liver images includes: comparing the pixel values of the segmented lesion to pixel values in a reference region, the reference region within the boundary of the liver and outside of the boundary of the lesion, in each image of the series of aligned liver images; and determining a classification of each sub-segment of the lesion as one of viable tissue, necrotic tissue, undefined tissue, and chemoembolized tissue based on a change in the pixel values within the sub-segment relative to the pixel values in the reference region across the series of aligned liver images. In some examples, outputting the analysis of the sub-segmented lesion includes outputting the classification of each sub-segment of the lesion as an annotated image of the sub-segmented lesion. In an example, the method further comprises determining a diagnostic score of the lesion based on an intensity profile of each pixel within the viable tissue sub-segment over the series of aligned liver images, and wherein outputting the analysis of the sub-segmented lesion includes outputting the diagnostic score.

An example system comprises a computed tomography (CT) system; a memory storing instructions; and a processor communicably coupled to the memory and, when executing the instructions, configured to: receive a plurality of images acquired by the CT system during a multi-phasic exam enhanced with a contrast agent; identify a boundary of an anatomical feature in at least one of the plurality of images via a deep learning model; determine a diagnostic score for the anatomical feature based on hypo- and hyper-enhancement of contrast agent within regions of the anatomical feature throughout the multi-phasic exam; and output the diagnostic score. In examples, the anatomical feature is a liver, and the processor, when executing the instructions, is further configured to: identify a boundary of a cancerous lesion within the liver via a random walker algorithm. In examples, the regions include regions of viable tissue within the lesion, and wherein the processor, when executing the instructions, is further configured to: create a reference region of interest (ROI) outside of the lesion and inside of the liver; statistically analyze the reference ROI to determine a mean value in each of the plurality of images; and sub-segment the regions of viable tissue within the lesion by generating a temporal profile of a change in brightness in each pixel of the lesion compared with the reference ROI across the plurality of images, the sub-segmented regions including a peripheral enhancement region. In an example, the multi-phasic exam includes an unenhanced phase, an arterial phase, a portal phase, and a delayed phase, and the processor, when executing the instructions, is further configured to: calculate a first probability of arterial phase hyper-enhancement of the contrast agent within the sub-segmented regions of viable tissue within the lesion; calculate a second probability of portal phase hypo-enhancement of the contrast agent within the sub-segmented regions of viable tissue within the lesion; calculate a third probability of portal phase hyper-enhancement of the contrast agent within the peripheral enhancement region; and determine the diagnostic score based on the first probability, the second probability, and the third probability.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
   acquiring a plurality of medical images over time during an exam;
   registering the plurality of medical images;
   segmenting an anatomical structure in one of the plurality of medical images after registering the plurality of medical images;
   identifying a boundary of a cancerous lesion of the anatomical structure;
   creating and characterizing a reference region of interest (ROI) outside of the lesion and inside of the anatomical structure in each of the plurality of medical images;
   determining characteristics of the anatomical structure by tracking pixel values of the segmented anatomical structure over time;
   sub-segmenting regions of viable tissue within the lesion by generating a temporal profile of a change in brightness in each pixel of the lesion compared with the reference ROI across the plurality of medical images, the sub-segmented regions including a peripheral enhancement region; and
   outputting the determined characteristics on a display device.

2. The method of claim 1, wherein registering the plurality of medical images includes applying rigid and non-rigid registrations to a source image and a target image, the source image and the target image selected from the plurality of medical images.

3. The method of claim 1, further comprising:
   after registering the plurality of medical images and segmenting the anatomical structure, segmenting a lesion within the anatomical structure.

4. The method of claim 3, wherein segmenting the anatomical structure includes using a convolutional neural network, and segmenting the lesion includes extracting and clustering textural features based on a received maximal axial diameter of the lesion, the textural features including at least one of a mean, a median, and a standard deviation of the pixel values within the segmented anatomical structure in each of the plurality of medical images.

5. The method of claim 3, wherein the exam is a multi-phasic contrast-enhanced computed tomography (CT) exam, and segmenting the anatomical structure includes segmenting a liver.

6. The method of claim 5, wherein the multi-phasic contrast-enhanced CT exam includes an unenhanced phase, an arterial phase after the unenhanced phase, a portal phase after the arterial phase, and a delayed phase after the portal phase, and the plurality of medical images include a first CT image of the liver obtained during the unenhanced phase, a second CT image of the liver obtained during the arterial phase, a third CT image of the liver obtained during the portal phase, and a fourth CT image of the liver obtained during the delayed phase.

7. The method of claim 5, wherein the reference ROI comprises tissue outside of the segmented lesion and within the segmented liver, wherein the characteristics of the anatomical structure include a tissue classification of each portion of the segmented lesion, and wherein determining the characteristics of the anatomical structure by tracking the pixel values of the segmented anatomical structure over time includes determining the tissue classification of each portion of the segmented lesion based on a value of each pixel within the portion relative to the reference ROI in each of the plurality of medical images.

8. The method of claim 7, wherein the tissue classification is one of necrotic, viable, chemoembolized, undefined, peripheral enhancement, and parenchymal.

9. The method of claim 8, wherein the characteristics of the anatomical structure further include an effect of a treatment, and determining the characteristics of the anatomical structure by tracking the pixel values of the segmented anatomical structure over time further includes determining the effect of the treatment by comparing the tissue classification of each portion of the segmented lesion from a first exam and with the tissue classification of each portion of the segment lesion from a second exam, the first exam performed before the treatment and the second exam performed after the treatment.

10. The method of claim 7, wherein the characteristics of the anatomical structure further include Liver Imaging Reporting and Data System (LI-RADS) scores, and determining the characteristics of the anatomical structure by tracking the pixel values of the segmented anatomical structure over time further includes:
determining arterial phase hyperenhancement (APHE), wash-out, and capsule probabilities of a contrast agent used in the multi-phasic contrast-enhanced CT exam based on the pixel values of the segmented lesion relative to the reference ROI in each of the plurality of medical images.

11. A method, comprising:
receiving a series of liver images from a multi-phasic exam;
aligning the series of liver images;
segmenting the liver and a lesion within the series of aligned liver images;
sub-segmenting the lesion based on changes in pixel values of the segmented lesion across the series of aligned liver images; and
outputting an analysis of the sub-segmented lesion,
wherein sub-segmenting the lesion based on the changes in pixel values of the segmented lesion across the series of aligned liver images includes:
comparing the pixel values of the segmented lesion to pixel values in a reference region, the reference region within the boundary of the liver and outside of the boundary of the lesion, in each image of the series of aligned liver images; and
determining a classification of each sub-segment of the lesion as one of viable tissue, necrotic tissue, undefined tissue, and chemoembolized tissue based on a change in the pixel values within the sub-segment relative to the pixel values in the reference region across the series of aligned liver images.

12. The method of claim 11, wherein the series of liver images include one liver image from each phase of the multi-phasic exam, and segmenting the liver includes:
defining a boundary of the liver in one image of the series of aligned liver images using a convolutional neural network; and
applying the boundary of the liver to each additional image in the series of aligned liver images.

13. The method of claim 12, wherein segmenting the lesion includes:
defining a boundary of the lesion within the boundary of the liver in the one image of the series of aligned liver images based on textural features of the one image, the textural features including at least one of a mean, a median, and a standard deviation of the pixel values within the boundary of the liver in the one image; and
applying the boundary of the lesion to each additional image in the series of aligned liver images.

14. The method of claim 11, wherein outputting the analysis of the sub-segmented lesion includes outputting the classification of each sub-segment of the lesion as an annotated image of the sub-segmented lesion.

15. The method of claim 14, further comprising, determining a diagnostic score of the lesion based on an intensity profile of each pixel within the viable tissue sub-segment over the series of aligned liver images, and wherein outputting the analysis of the sub-segmented lesion includes outputting the diagnostic score.

16. A system, comprising:
a computed tomography (CT) system;
a memory storing instructions; and
a processor communicably coupled to the memory and, when executing the instructions, configured to:
receive a plurality of images acquired by the CT system during a multi-phasic exam enhanced with a contrast agent;
identify a boundary of an anatomical feature in at least one of the plurality of images via a deep learning model;
determine a diagnostic score for the anatomical feature based on hypo- and hyper-enhancement of contrast agent within regions of the anatomical feature throughout the multi-phasic exam; and
output the diagnostic score,
wherein the anatomical feature is a liver, and the processor, when executing the instructions, is further configured to:
identify a boundary of a cancerous lesion within the liver via a random walker algorithm,
wherein the regions include regions of viable tissue within the lesion, and wherein the processor, when executing the instructions, is further configured to:
create a reference region of interest (ROI) outside of the lesion and inside of the liver;
statistically analyze the reference ROI to determine a mean value in each of the plurality of images; and
sub-segment the regions of viable tissue within the lesion by generating a temporal profile of a change in brightness in each pixel of the lesion compared with the reference ROI across the plurality of images, the sub-segmented regions including a peripheral enhancement region.

17. The system of claim 16, wherein the multi-phasic exam includes an unenhanced phase, an arterial phase, a portal phase, and a delayed phase, and the processor, when executing the instructions, is further configured to:
calculate a first probability of arterial phase hyper-enhancement of the contrast agent within the sub-segmented regions of viable tissue within the lesion;
calculate a second probability of portal phase hypo-enhancement of the contrast agent within the sub-segmented regions of viable tissue within the lesion;

calculate a third probability of portal phase hyper-enhancement of the contrast agent within the peripheral enhancement region; and
determine the diagnostic score based on the first probability, the second probability, and the third probability.

* * * * *